(12) United States Patent
Peck et al.

(10) Patent No.: US 6,709,820 B2
(45) Date of Patent: *Mar. 23, 2004

(54) **MATERIALS AND METHODS FOR DETECTION OF *OXALOBACTER FORMIGENES***

(75) Inventors: Ammon B. Peck, Gainesville, FL (US); Harmeet Sidhu, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/829,094

(22) Filed: Apr. 9, 2001

(65) Prior Publication Data

US 2002/0081681 A1 Jun. 27, 2002

Related U.S. Application Data

(63) Continuation of application No. 08/936,094, filed on Sep. 23, 1997, now Pat. No. 6,214,980, which is a continuation-in-part of application No. 08/883,610, filed on Jun. 26, 1997, now Pat. No. 6,090,628, which is a continuation-in-part of application No. 08/717,587, filed on Sep. 27, 1996, now Pat. No. 5,912,125, which is a continuation-in-part of application No. 08/493,197, filed on Jun. 20, 1995, now Pat. No. 5,837,833, which is a continuation-in-part of application No. 08/262,424, filed on Jun. 20, 1994, now Pat. No. 5,604,111.

(51) Int. Cl.[7] ........................ C12Q 1/68; C12P 19/34; C07H 21/02; C07H 21/04
(52) U.S. Cl. ...................... 435/6; 435/91.1; 435/91.2; 536/23.1; 536/24.3; 536/24.33
(58) Field of Search .................. 435/6, 91.1, 91.2; 536/23.1, 24.3, 24.33

(56) References Cited

U.S. PATENT DOCUMENTS 4,455,371 A 6/1984 Richardson et al. .......... 435/25
4,539,118 A 9/1985 Crider ........................ 210/683
5,043,272 A 8/1991 Hartley ........................ 435/91
5,213,961 A 5/1993 Bunn et al. ..................... 435/6
5,219,727 A 6/1993 Wang et al. .................... 435/6
5,635,616 A 6/1997 Olsen et al. ............... 536/23.1

FOREIGN PATENT DOCUMENTS

WO 9535377 12/1995

OTHER PUBLICATIONS

Hodgkinson, A. (1970) "Determination of Oxalic Acid in Biological Material" *Clinical Chemistry* 16(7):547–557.

Curhan, Gary C. M.D. et al. (1993) "A Prospective Study of Dietary Calcium and Other Nutrients and the Risk of Symptomatic Kidney Stones" *N.E.J. Med.* 328(12):833–838.

(List continued on next page.)

*Primary Examiner*—Jezia Riley
(74) *Attorney, Agent, or Firm*—Saliwanchik, Lloyd & Saliwanchik

(57) ABSTRACT

The subject invention concerns the novel use of formyl-CoA transferase enzyme together with oxalyl-CoA decarboxylase enzyme for the detection and measurement of oxalate in biological samples. The use of the enzyme system according to the subject invention results in the conversion of oxalate into carbon dioxide and formate. Because the production of formate is directly correlated to the concentration of oxalate present in a sample, the determination of the resulting formate concentration provides an accurate, sensitive and rapid means for detecting even low levels of oxalate. The subject invention further concerns the cloning, sequencing and expression of the genes that encode the formyl-CoA transferase enzyme and the oxalyl-CoA decarboxylase enzyme of *Oxalobacter formigenes*. The subject invention also concerns methods for detecting the presence of *Oxalobacter formigenes* organisms in a sample, and the polynucleotide probes and primers used in the detection method.

49 Claims, 17 Drawing Sheets

OTHER PUBLICATIONS

Costello, J. et al. (1976) "An Enzymatic Method for the Spectrophotometric Determination of Oxalic Acid" *J. Lab. Clin. Med.* 87(5):903–908.

Baetz, A.L. and Allison, M.J. (1989) "Purification and Characterization of Oxalyl–Coenzyme A Decarboxylase from *Oxalobacter formigenes*" *Journal of Bacteriology* 171(5):2605–2608.

Baetz, A.L. and Allison, M.J. (1990) "Purification and Characterization of Formyl–Coenzyme A Transferase from *Oxalobacter formingenes*" *Journal of Bacteriology* 172(7):3537–3540.

Yriberri, J. and Posen, S. (1980) "A Semi–Automatic Enzymatic Method for Estimating Urinary Oxalate" *Clin. Chem.* 26(7):881–884.

Lung, H.Y. et al. (1994) "Molecular Cloning, DNA Sequence and Gene Expression of the Oxalyl–Coenzyme A Decarboxylase Gene, oxc, from the Bacterium *Oxalobacter formingenes*" *Journal of Bacteriology* 176(8):2468–2472.

Allen, L.C. et al. (1989) "An Enzymatic Method for Oxalate Automated with the Cobas Fara Centrifugal Analyzer" *Clin. Chem.* 35(10):2098–2100.

Li, M.G. and Madappally, M.M. (1989) "Rapid Enzymatic Determination of Urinary Oxalate" *Clin. Chem.* 35(12):2330–2333.

Santamaria, J.R. et al. (1993) "Comparative Study of Two Commerical Enzymatic Kits for Determining Oxalate Concentrations in Urine" *Clin. Biochem.* 26:93–96.

Infantes, J.A. et al. (1991) "Kinetic–Enzymatic Determination of Oxalate in Urine by Flow Injection Analysis with Double Stopped Flow" *Analytica Chimica Acta.* 242:179–183.

Costello, J.F. and Smith, M. (1992) "Determination of Evolved $^{14}CO_2$ in Decarboxylase Reactions with Application to Measurement of [$^{14}C$]Oxalic Acid" *Analytical Biochemistry* 202:337–339.

Binette, Y. and Durocher, J.–G. (1985) "Le Dosage des Oxalates Urinaires: Comparaison de Trois Methodes" *Ann. Biochem. Clin. Que.* 24(3):93–96.

Hatch, M. and Freel, R.W. (1996) "Oxalate Transport Across Intestinal and Renal Epithelia" *Calcium Oxalate in Biological Systems*, pp. 217–238, CRC Press, Boca Raton, FL.

Dawson, K.A. et al. (1980) "Isolation and Some Characteristics of Anaerobic Oxalate–Degrading Bacteria from the Rumen" *Applied and Environmental Microbiology* 40(4):833–839.

Anderson, J.T. et al. (1993) "Insulin–Dependent Diabetes in the NOD Mouse Model II. β Cell Destruction in Autoimmune Diabetes is a $T_{H2}$ and not a $T_{H1}$ Mediated Event" *Autoimmunity* 15:113–122.

Stacy–Phipps, S. et al. (1995) "Multiplex PCR Assay and Simple Preparation Method for Stool Specimens Detect Enterotoxigenic *Escheria coli* DNA During Course of Infection" *Journal of Clinical Microbiology* 33(5):1054–1059.

Stragtagene Catalog (1988) Stratagene Cloning Systems, La Jolla, CA, p. 39.

New England Biolabs Catalog (1986) Beverly, MA, p. 61.

Lung et al. (1991) "Cloning and Expression of the Oxalyl–CoA Decarboxylase Gene from the Bacterium, *Oxalobacter formingenes*: Prospects for Gene Therapy to Control Ca–Oxalate Kidney Stone Formation" *American Journal of Kidney Diseases* 12(4):381–385.

Allison, M.J. et al. (1985) "*Oxalobacter formigenes* gen. nov., sp. nov.: Oxalate Degrading Bacteria that Inhabit the Gastrointestinal Tract" *Arch. Microbiol.* 141:1–7.

Jensen, N.S. et al. (1994) "Studies on the Diversity Among Anaerobic Oxalate–Degrading Bacteria now in the Species *Oxalobacter formingenes*" *Abst. Ann. Mtg. Amer. Soc. Microbial.*, pp. 1–29.

Tarnuzzer, R.W, et al. (1996) "Competitive RNA Templates for Detection and Quantitation of Growth Factors, Cytokines, Extracellular Matrix Components and Matrix Metalloproteinases by RT–PCR" *Bio Techniques* 20:670–674.

Allison, M.J. et al. (1986) "Oxalate Degradation by Gastrointestinal Bacteria from Humans" *J Nutr.* 116:455–460.

Argenzio, R.A. et al. (1988) "Intestinal Oxalate Degrading Bacteria Reduce Oxalate Absorption and Toxicity in Guinea Pigs" *J Nutr.* 118:787–791.

Daniel, S. et al. (1987) "Microbial Degradation of Oxalate in the Gastrointestinal Tracts of Rats" *Appl Environ Microbiol* 53:957–964.

Jordan, J.A. and Durso, M.B. (1996) "Rapid Speciation of the Five Most Medically Relevant Candida Species Using PCR Amplification and a Microtitre Plate–Based Detection System" *Mol Diagnosis* 1:51–58.

Smith, R.L. et al. (1985) "Isolation of Anaerobic Oxalate–Degrading Bacteria from Fresh Water Lake Sediments," *Arch Microbiol* 141:8–13.

FIG. 2A

```
R  L  E  R  T  G  I  L  A  E  Y  P  Q  A  Q  P  N  F  A  F  D  R  D  G  N  P  L  S  F  N  N  I  T  S  V  P
CGTCTGGAAAGAACGGGCATTCTGGCTGAATACCCACAGGCTCAGCCTAACTTTGCCTTCGACAGAGACGGTAACCCACTGTCCTTCGACAACATCACTTCCGTTCCA  864

R  G  G  N  A  G  G  G  E  P  G  W  M  L  K  C  K  G  W  E  T  D  A  D  S  Y  Y  F  T  I  A  A  N  M
CGTGGTGGTAACGCAGGTGGCGGCGGCGAGCCAGGCTGGATGCTGAAATGTAAAGGTTGGGAAACCGATGCGGACTCCTACGTTTACTTCACCATCGCTGCAAACATG  972

W  P  Q  I  C  N  M  I  D  K  P  E  W  K  D  D  P  A  Y  N  T  F  E  G  R  V  D  K  L  M  D  I  F  S  F  I
TGGCCACAGATCTGCAACATGATCGACAAGCCAGAGTGGAAAGACGACCCAGCCTACAACACATTCGAAGGTCGTGTTGACAAGCTGATGGACATCTTCTCCTTCATC  1080

E  T  K  F  A  D  K  D  K  F  E  V  T  E  W  A  A  Q  Y  G  I  P  C  G  P  V  M  S  M  K  E  L  A  H  D  P
GAAACCAAGTTCGCTGACAAAGACAAATTCGAAGTTACCGAATGGGCTGCCCAGTACGGCATTCCTTGCGGTCCGGTCATGTCCATGAAAGAACTGGCTCACGATCCT  1188

S  L  Q  K  V  G  T  V  V  E  V  V  D  E  I  R  G  N  H  L  T  V  G  A  P  F  K  F  S  G  F  Q  P  E  I  T
TCCCTGCAGAAAGTTGGTACCGTCGTTGAAGTTGTGTCGACGAAATTCGTGTGGTAACCACCTGACCGTTGGCGCCGTTCAAATTCTCCGGATTCCAGCCGGAAATTACC  1296

R  A  P  L  L  G  E  H  T  D  E  V  L  K  E  L  G  L  D  D  A  K  I  K  E  L  H  A  K  Q  V  ter
CGTGCTCCGCTGTTGGGCGAACATACAGACGAAGTTCTGAAAGAACTGGGTCTTGACGATGCCAAGATCAAGGAACTGCATGCAAAACAGGTAGTTTGATCCGTCAGA  1404

CTTTCTGGGCAAAACGGCACTCTCCGGAGTGCCGTTTTTTGTCACACGAAACCTAATCAAACAAGCACGTCAATGATTCCACATCATTGCGGCCACATTCATCCTTC
                            ————————————————————                                                       1416
GGGTCATTACTG.................
```

FIG. 2B

Bolded letters represent amino acid residues determined by N-terminal protein sequencing

FIG. 3A

```
      -180          -172              -139              -124              -100               -91             -81
            ATTTGTTTAAATTGACCTGAATCAATATTGCCGGATTGATCTAGGTCAATGATGAATTGACTTATGTCAATGGTGCCAAATTGACCTAGGTCAACGG
                          -51                       -32                       -14                             20
       -80                                                                                              M  S  N  D  D  N  V
            GATTTTTAAAGGGTATGCGGCATACTCGGAATTGACGTTAAACAACGTTATCAAAACCAACCAAAGAAGAAAGGTATTACTCATGAGTAACGACGACAATGT   120
        21   E  L  T  D  G  F  H  V  L  I  D  A  L  K  M  N  D  I  D  T  M  Y  G  V  V  G  I  P  I  T  N  L  A
            AGAGTTGACTGATGGCTTTCATGTTTTGATCGATGCCCTGAAAATGAATGACATCGATACCATGTATGGTGTTGTCGGCATTCCTATCACGAACCTGGCT   220
       121   R  M  W  Q  D  D  G  Q  R  F  Y  S  F  R  H  E  Q  H  A  G  Y  A  A  S  I  A  G  Y  I  E  G  K  P
            CGTATGTGGCAAGATGACGGTCAGCGTTTTTACAGCTTCCGTCACGAACAAACACGCAGGTTATGCAGCTTCTATCGCCGGTTACATCGAAGGAAAACCTG   320
       221   G  V  C  L  T  V  S  A  P  G  F  L  N  G  V  T  S  L  A  H  A  T  T  N  C  F  P  M  I  L  L  S  G  S
            GCGTTTGCTTGACCGTGTCCGCCCCTGGCTTCCTGAACGGGGTCACTTCCCTGGCTCATGCAACCACCAACTGCTTCCCAATGATCCTGTTGAGCGGGGTC   420
       321   S  R  E  I  V  D  L  Q  Q  G  D  Y  E  E  M  D  Q  M  N  V  A  R  P  H  C  K  A  S  F  R  I  N
            CAGTGAACGTGAAATCGTCGATTTCCAAGACGGCGATTACGAAGACATGGATCAGATGAATGTTGCACGTCCACACTGCAAAGCTTCTTTCGTATCAAC   520
       421   S  I  K  D  I  P  I  G  I  A  R  A  V  R  T  A  V  S  G  R  P  G  G  V  Y  V  D  L  P  A  K  L  F
            AGCATCAAAGACATTCCAATCGGTATCGCTCGTGCAGTTCGCACCGCTGTATCCGGTAGGCCAGGTGGTGTTTACGTTGACTTCCCAGCAAAACTGTTCG   620
       521   G  Q  T  I  S  V  E  E  A  N  K  L  L  F  K  P  I  D  P  A  P  A  Q  I  P  A  E  D  A  I  A  R  A  A
            GTCAGACCATTTCTGTAGAAGAAGCTAACAAACTGCTCTTCAAACCAATCGATCCAGCTCCGGCACAGATTCCTGCTGAAGACGCTATCGCTCGGCCTGC   720
       621   D  L  I  K  N  A  K  R  P  V  I  M  L  G  K  G  A  A  Y  A  Q  C  D  D  E  I  R  A  L  V  E  E  T
            TGACCTGATCAAGAACGCCAAACGTCCAGTTATCATGCTGGGTAAAGGCGCTGCATACGCACAGTGCGACGACGAAATCCGGCACTGGTTGAAGAAACC   820
       721   G  I  P  F  L  P  M  G  M  A  K  G  L  L  P  D  N  H  P  Q  S  A  A  T  R  A  F  A  L  A  Q  C
            GGCATCCCATTCCTGCCAATGGGTATGGCTAAAGGCCTGCTGCCTGACAACCATCCACAATCCGCTGCTACTCGTGCTTTCGCACTGGCACAGTGTG   920
       821   D  V  C  V  L  G  A  R  L  N  W  L  M  Q  H  G  K  T  W  G  D  E  L  K  K  Y  V  Q  I  D  I
            ACGTTTGCGTACTGGGCGCTCGTCTGAACTGGCTGATGCAGCACGGCAAAACCTGGGGCGACGAACTGAAGAAATACGTTCAGATCGACAT
```

FIG. 3B

```
      Q  A  N  E  M  D  S  N  Q  P  I  A  A  P  V  V  G  D  I  K  S  A  V  S  L  L  R  K  A  L  K  G  A
 921  CCAGGCTAACGAAATGGACAGCAACCAGCCTATCGCTGCACCAGTTGTTGGTGACATCAAGTCCGCGGTTTCCCTGCTCCGCAAAGCACTGAAAGGCGCT  1020
      P  K  A  D  A  E  W  T  G  A  L  K  A  K  V  D  G  N  K  A  K  L  A  G  K  M  T  A  E  T  P  S  G
1021  CCAAAAGCTGACGCTGAATGGAACCGGCTGAAAGCCAAAGTTGACGGCAACAAAGCCAAACTGGCTGGCAAGATGACTGCCGAAACCCCATCCGGAA  1120
      M  M  N  Y  S  N  S  L  G  V  V  R  D  F  M  L  A  N  P  D  I  S  L  V  N  E  G  A  N  A  L  D  N  T
1121  TGATGAACTACTACTCCAATTCCCTGGGCGTTGTTCGTGACTTCATGCTGGCAAATCCGGATATTTCCCTGGTTAACGAAGGCGCTAATGCACTCGACAACAC  1220
      R  M  I  V  D  M  L  K  P  R  K  R  L  D  S  G  T  W  G  V  M  G  I  G  M  G  Y  C  V  A  A  A
1221  TCGTATGATTGTTGACATGCTGAAACCGCGCAAACCACCGCGTCTTGACTCCGGTACCTGGGGTGTTATGGGCTACTGCGTTGCTGCAGCTGCT  1320
                                                            [----------TPP Binding Motif----------
      V  T  G  K  P  V  I  A  V  E  G  D  S  A  F  G  F  S  G  M  E  L  E  T  I  C  R  Y  N  L  P  V  T
1321  GTTACCGGCAAACCGGTTATCGCTGTTGAAGGCGATAGCGCATTCGGTTTCTCCGGTATGGAACTGGAAACCATCTGCCGTTACAACCTGCCAGTTACCG  1420
                      ----------]
      V  I  I  M  N  N  G  G  I  Y  K  G  N  E  A  D  P  Q  P  G  V  I  S  C  T  R  L  T  R  G  R  Y  D  M
1421  TTATCATCATGAACAATGGGGTATCTATAAAGGTAACGAAGCAGATCCACAACCAGGCGTTATCTCCTGTACCCGTCTGACCCGTGGTCGTTACGACAT  1520
      M  M  E  A  F  G  G  K  G  Y  V  A  N  T  P  A  E  L  K  A  A  L  E  E  A  V  A  S  G  K  P  C  L
1521  GATGATGGAAGCATTTGGCGGTAAAGGTTATGTTGCCAATACTCCAGCTGAACTGAAAGCTGCTCTGGAAGAAGCTGTTGCTTCCGGCAAACCATGCCTG  1620
                                                                                              1705
      I  N  A  M  I  D  P  D  A  G  V  G  S  G  R  I  K  S  L  N  V  V  S  K  V  G  K  K
1621  ATCAACGCGATGATCGATCCAGACGCTGGTGTCGAATCTGGCCGTATCAAGAGCCTGAACGTTGTAAGTAAAGTTGGCAAGAAATAATTAGCCCAACTTT  1720
                                                                                    1758
                                                                                                      1820
1721  GATGACCGGTTACGACCGGTCACATAAAGTGTTCGAATGCCCTTCAAGTTACTTGAAGGCATTTTTTTACTTGCAGTTTATAAACAGGAAAAATTGT
                                                                           1908
1821  ATTCAGAGCGGAAAGCACGAGATTAAGCCACGAGAAACAGATTAAGCCACGAGAAACACATTTTAAAGCTGGCTTTT
```

FIG. 9A

```
         -60   (AP34)                                            1   M   S   N   D   D   N   V   E   L   T   D   G   F   H   V   L   I   51
              ..ATACTTCGGAATTGACGTTAAACA......................ATGAGTAACGACGACAATGTAGAGTTGACTGATGGCTTTCATGTTTTGATC...
       OxB                       ..TAAACA......................ATGAGTAACGACGACAATGTAGAGTTGACTGATGGCTTTCATGTTTTGATC...
       HC1                       ..TAAACA......................ATGAGTAACGACGACAATGTAGAGTTGACTGATGGCTTTCATGTTTTGATC...
 gpI   HOxCC12                   ..TAAACA......................ATGAGTAACGACGACAATGTAGAGTTGACTGATGGCTTTCATGTTTTGATC...
       HOxHM18                   ..TAAACA......................ATGAGTAACGACGACAATGTAGAGTTGACTGATGGCTTTCATGTTTTGATC...
       HOxRA                     ..TAAACA......................ATGAGTAACGACGACAATGTAGAGTTGACTGATGGCTTTCATGTTTTGATC...
       HOxUK90                   ..TAAACA......................ATGAGTAACGACGACAATGTAGAGTTGACTGATGGCTTTCATGTTTTGATC...
                                                                                                      ‡     ‡ ‡‡
       HOxRW                     ..TGAACA......................ATGAGTAACGACGACAATGTAGAGTTGACTGATGGCTTTCATGTGTTAAAG...
       HOxBLS                    ..TGAACA......................ATGAGTAACGACGACAATGTAGAGTTGACTGATGGCTTTCATGTGTTAAAG...
                                     ‡                                                                 ‡   ‡
       BA1                       ..TAAACA......................ATGAGTAACGACGACAATGTAGAGTTGACTGATGGCTTTCATGTGCTGATG...
 gpII  OxK                       ..TAAACA......................ATGAGTAACGAAGACAATGTAGAGACAATGTAGAGTTGACTGATGGCTTTCATGTGCTGATG...
                                     ‡                                         ‡
       HOxUK5                    ..TGAACA......................ATGAGTAACGAAGACAATGTAGAGTTGACTGATGGCTTTCATGTGCTGATG...
       HOxUK88                   ..TGAACA......................ATGAGTAACGAAGACAATGTAGAGTTGACTGATGGCTTTCATGTGCTGATG...
                                                                                                                ‡
       HOxHS                     ..TGAACA......................ATGAGTAACGAAGACAATGTAGAGTTGACTGATGGCTTTCATGTGCTGAAG...

115   L   A   R   M   W   Q   D   D   G   Q   R   F   Y   S   F   R   H   E   Q   H   A   G   Y   A   A   S   192
       OxB    .....CTGGCTCGTCGTATGTGGCAAGATGACGGTCAGCGTTTTTACAGCTTCCGTCACGAACAACACGCAGGTTATGCAGCTTCT
       HC1    .....CTGGCTCGTCGTATGTGGCAAGATGACGGTCAGCGTTTTTACAGCTTCCGTCACGAACAACACGCAGGTTATGCAGCTTCT
                                                  ‡
 gpI   HOxCC12 ....CTGGCTCGTCGTATGTGGCAAGATGACGGTCAGCGTTTTTACAGCTTCCGTCACGAACAACACGCAGGTTATGCAGCTTCT
       HOxHM18 ....CTGGCTCGTCGTATGTGGCAAGATGACGGTCAGCGTTTTTACAGCTTCCGTCACGAACAACACGCAGGTTATGCAGCTTCT
                                                  ‡                ‡
       HOxRA  .....TTGGCTCGTCGTATGTGGCAAGATGACGGTCAGCGTTTTTACAGCTTCCGTCATGAACAACACGCTACGCAGCATCT
       HOxUK90 ....TTGGCTCGTCGTATGTGGCAAGATGACGGTCAGCGTTTTTACAGCTTCCGTCATGAACAACACGCTACGCAGCATCT
                                                                              ‡          ‡
```

FIG. 9B

```
                      ↕            ↕       ↕  ↕↕        ↕↕↕    ↕             ↕             ↕        ↕              ↕      ↕  ↕     ↕
HOxRW       ......CTGGCCCCGTCGTTGGGAACAGGATGGTCAGAAGTTCTATAGCTTCCGCCACGAACAGCACGCTGGCTATGCTGCCTCT
                                                                                                                         ↕  ↕     ↕
HOxBLS      ......CTGGCCCCGTCGTTGGGAACAGGATGGTCAGAAGTTCTATAGCTTCCGCCACGAACAGCACGCTGGCTATGCTGCCTCT
                                                                                                      ↕
BA1         ......CTGGCCCCGTCGTTGGGAACAGGATGGTCAGAAGTTCTACAGCTTCCGCCACGAACAGCACGCTGGCTACGCCGCATCC
                                                                                                                 ↕       ↕
OxK         ......CTGGCCCCGTCGTTGGCAACAGGATGGTCAGAAGTTCTACAGCTTCCGCCACGAGCAGCAGCATGCTGGCTACGCTGCATCC
gpII
HOxUK5      ......CTGGCCCCGTCGTTGGGAACAGGATGGTCAGAAGTTCTACAGCTTCCGCCACGAGCAGCAGCATGCTGGCTACGCTGCATCC
                                                                                                                                 ↕
HOxUK88     ......CTGGCCCCGTCGTTGGGAACAGGATGGTCAGAAGTTCTACAGCTTCCGCCACAAGCAGCAGCATGCTGGCTACGCTGCATCC
                                                                                                                        ↕
HOxHS       ......CTGGCTCGTCGTTGGGAACAGGATGGTCAGAAGTTCTACAGCTTCCGCCACGACAACATGCTGGCTACGCTGCTTCC 193        (HS2)               (codon deletion)                                       (AP21)       454
              I A G Y I E G                    K P G            ⇒                     R I N S I K D I P P I G I A
OxB         ATCGCCGGTTACATCGAAGGA.........AAACCTGGCG.......................CGTATCAACAGCATCAAAGACATTCCAATCGGTATCGCTC..
HC1         ATCGCCGGTTACATCGAAGGA.........AAACCTGGCG.......................CGTATCAACAGCATCAAAGACAT.............
HOxCC12     ATCGCCGGTTACATCGAAGGA.........AAACCTGGCG.......................CGTATCAACAGCATCAAAGACAT.............
gpI  HOxHM18     ATCGCCGGTTACATCGAAGGA.........AAACCTGGCG.......................CGTATCAACAGCATCAAAGACAT.............
HOxRA       ATCGCCGGTTACATCGAAGGA.........AAACCTGGCG.......................CGTATCAACAGCATCAAAGACAT.............
HOxUK90     ATCGCCGGTTACATCGAAGGA.........AAACCTGGCG.......................CGTATCAACAGCATCAAAGACAT.............
                    ↕      ↕   ↕↕  ↕↕↕↕
HOxRW       ATTGCCGGCTACATTCAGGGCGACAAACCTGGCG.......................CGTATCAACAGCAGCATCAAAGACATAT........
HOxBLS      ATTGCCGGCTACATTCAGGGCGACAAACCTGGCG.......................CGTATCAACAGCAGCATCAAAGACATAT........
                        ↕ ↕↕ ↕
BA1         ATTGCTGGCTACATCCAGGCCGACAAATAAACCTGGCG...................CGTATCAACAGCAGCATCAAGGACAT.........
                        ↕↕ ↕↕↕↕↕     ↕
OxK         ATTGCTGGCTACATCCAGGGCGACAAACCAGTG........................CGTATCAACAGCAGCATCAAGGACAT.........
gpII HOxUK5      ATTGCTGGCTACATCCAGGGCGACAAACCAGTG........................CGTATCAACAGCAGCATCAAGGACAT.........
HOxUK88     ATTGCTGGCTACATCCAGGGCGACAAACCAGTG........................CGTATCAACAGCAGCATCAAGGACAT.........
                                                                                                   ↕
HOxHS       ATCGCTGGTTACATCCATGGCGACAAACCAGTG........................CGTATCAACAGCAGCATCAATGACAT.........
```

MATERIALS AND METHODS FOR DETECTION OF *OXALOBACTER FORMIGENES*

CROSS-REFERENCE TO A RELATED APPLICATIONS

This application is a continuation of U.S. application Ser. No. 08/936,094, filed Sep. 23, 1997, now U.S. Pat. No. 6,214,980; which is a continuation-in-part of patent application Ser. No. 08/883,610, filed Jun. 26, 1997, now U.S. Pat. No. 6,090,628; which is a continuation-in-part of patent application Ser. No. 08/717,587, filed Sep. 27, 1996, now U.S. Pat. No. 5,912,125; which is a continuation-in-part of patent application Ser. No. 08/493,197, filed Jun. 20, 1995, now U.S. Pat. No. 5,837,833; which is a continuation-in-part of patent application Ser. No. 08/262,424, filed Jun. 20, 1994, now U.S. Pat. No. 5,604,111.

This invention was made with government support under National Institutes of Health Grant No. DK 20586. The government has certain rights in this invention.

FIELD OF INVENTION

The present invention relates to novel assay methods and devices for determining the presence or concentration of oxalate in a sample; Oxalobacter genes encoding enzymes required for the catabolism of oxalate; and materials and methods for detecting and identifying *Oxalobacter formigenes* in a sample.

BACKGROUND OF THE INVENTION

Oxalic acid (Oxalate) is a highly toxic natural by-product of catabolism in vertebrate animals and many consumable plants. Unfortunately, a significant portion of humans are unable to properly metabolize oxalate, a condition which may result in the formation of kidney stones in those persons. It is estimated that 70% of all kidney stones are composed of some amount of oxalate. Approximately 12 percent of the U.S. population will suffer from a kidney stone at some time in their lives, and the incidence is rising not only in the United States, but also in Sweden and Japan (Curhan, 1993). Moreover, although a healthy person breaks down or excretes sufficient quantities of oxalate to avoid excessive accumulation of oxalate in the tissues, a number of disease states are known to be associated with malfunctions of oxalate metabolism, including pyridoxine deficiency, renal failure and primary hyperoxaluria, a metabolic genetic disorder that results in the excessive deposition of oxalate in the kidneys.

Persons suffering from and at risk for developing kidney stones, as well as patients with lipid malabsorption problems (e.g., sprue, pancreatic insufficiency, inflammatory intestinal disease, bowel resection, etc.), tend to have elevated levels of urinary oxalate, a fact that has been exploited as a means for identifying individuals at risk. While elevated levels of oxalate may be present in urine, detecting elevated levels of oxalate in serum has not been routine due to the difficulty in detecting the low levels of oxalate present in serum.

Most previous methods for measuring oxalate in a biological sample first require the isolation of the oxalate by precipitation, solvent extraction, or an ion-exchange absorption (Hodgkinson, 1970). Quantitation of the isolated oxalate may be determined by any one of several methods including colorimetry, fluorometry, gas-liquid chromatography or isotope dilution techniques. Because many of the oxalate isolation techniques used in these analytical methods are not quantitative, it is normally necessary to correct for the low recovery of oxalate by adding a $^{14}$C-labeled oxalic acid internal standard, which further complicates the analytical method. All these methods are laborious, and consequently expensive because of the amount of skilled laboratory technician time which must be employed. In addition, isolation of the oxalate may require relatively large sample volumes for starting material.

Recently, several advances in the detection and quantitation of oxalate have been made through the use of (a) oxalate degrading enzymes and (b) high performance liquid chromatography. One commercially-available enzymatic test (Sigma Chemical Company, St. Louis, Mo.) employs oxalate oxidase to oxidize oxalate to carbon dioxide and hydrogen peroxide. The hydrogen peroxide produced can then be measured colorimetrically in a second enzymatic reaction in the presence of peroxidase.

In another enzymatic method for measuring oxalate, oxalate decarboxylase is used to convert oxalate to carbon dioxide and formate. The resultant carbon dioxide can be measured manometrically, by the pH change in a carbon dioxide trapping buffer or by the color change in a pH indicator buffer. Whatever method of carbon dioxide assay is adopted, the time required for diffusion and equilibration of carbon dioxide is much longer than is desirable for a rapid analytical method.

Alternatively, the formate produced by the action of oxalate decarboxylase can be assayed with formate dehydrogenase in an NAD/NADH coupled reaction, as described in Costello, 1976 and Yriberri, 1980. This method is both cumbersome and time-consuming because oxalate decarboxylase and formate dehydrogenase differ in their optimum pH requirements, thus necessitating a pH adjustment during the analysis.

Another commercially available enzymatic test (Boehringer Mannheim) cleaves oxalate to formate and carbon dioxide, then oxidizes the formate to bicarbonate by NAD in the presence of the enzyme formate dehydrogenase. The amount of NADH is determined by means of its absorbance at 334, 340, or 365 nm. Another test ("STONE RISK" by Mission Pharmacal) measures oxalate as a part of a battery of tests for kidney stones.

*Oxalobacter formigenes* is a recently discovered, oxalate-degrading obligately anaerobic bacterium residing primarily in the intestines of vertebrate animals, including man (Allison et al., 1986). Although the first isolates of *O. formigenes* were cultured from sheep rumen (Dawson et al., 1980), additional strains have now been isolated from fecal contents of rats, guinea pigs and pigs (Argenzio et al., 1988, Daniel et al., 1987), fecal samples from man (Allison et al., 1985), and anaerobic aquatic sediments (Smith et al., 1985). This bacterium is unique among oxalate-degrading organisms having evolved a total dependence on oxalate metabolism for energy (Dawson et al., 1980). Recent evidence suggests that *Oxalobacter formigenes* has an important symbiotic relationship with vertebrate hosts by regulating oxalic acid absorption in the intestine as well as oxalic acid levels in the plasma (Hatch and Freel, 1996). Studies by Jensen and Allison (1994) comparing various *O. formigenes* isolates revealed only limited diversity of their cellular fatty acids, proteins, and nucleic acid fragments. Based on these comparisons, strains of *O. formigenes* have been divided into two major subgroups. In general, group I strains have shown limited intragroup diversity, while group II strains have shown greater intragroup diversity.

Special conditions are required to culture *O. formigenes* and their detection is based generally on the appearance of zones of clearance of calcium oxalate crystals surrounding colonies (Allison et al., 1986). Assays based on the appearance of zones of clearance of calcium-oxalate crystals surrounding bacterial colonies (Allison et al., 1985) or degradation of oxalate in culture media measured by calcium-chloride precipitation (Dawson et al., 1980) fail to confirm the oxalate-degrading bacteria as Oxalobacter.

As illustrated above, the currently existing assays for oxalate suffer from numerous problems, including cost, inaccuracy, reliability, complexity, and lack of sensitivity. Accordingly, it is an object of the subject invention to provide a simple, accurate, and sensitive assay for the detection of low levels of oxalate in a biological sample.

The current methods for culturing and identifying the presence of *Oxalobacter formigenes* are technically demanding and time consuming, and therefore, are not suitable for rapid and specific identification of *O. formigenes*, particularly for clinical diagnostics. Accordingly, another object of the subject invention is to provide a rapid, accurate polynucleotide probe-based assay for the detection of *O. formigenes*.

BRIEF SUMMARY OF THE INVENTION

The subject invention concerns the cloning, sequencing, and expression of the formyl-CoA transferase (frc) and the oxalyl-CoA decarboxylase (oxc) genes of *Oxalobacter formigenes*, and the use of the enzymes to detect the presence of oxalate in a sample. The assay of the subject invention provides, for the first time, a rapid, sensitive method to detect even very low concentrations of oxalate in biological samples. Advantageously, the biological samples in which oxalate can be detected include both urine and serum samples. The enzyme system used according to the subject invention converts oxalate to carbon dioxide and formate. In a preferred embodiment of the subject invention, the production of formate is then measured calorimetrically. This assay provides a sensitive, accurate and convenient means for detecting oxalate.

A further aspect of the subject invention is the discovery of the *O. formigenes* genes which encode the formyl-CoA transferase and the oxalyl-CoA decarboxylase enzymes. The discovery of these genes makes it possible to efficiently produce large quantities of pure formyl-CoA transferase and oxalyl-CoA decarboxylase for use in the assay of the subject invention or other appropriate application.

The subject invention further concerns a dipstick device for the detection and quantitation of oxalate in a sample. The dipstick device comprises the oxalyl-CoA decarboxylase and formyl-CoA transferase enzymes of the present invention immobilized on a carrier matrix. A detectable signal is generated on the dipstick if oxalate is present in the sample.

The subject invention also provides a means for detecting the presence of *Oxalobacter formigenes* organisms in a sample. The method of detection provided for herein involves polynucleotide probes which can be used to identify *Oxalobacter formigenes*.

The subject invention also concerns the polynucleotide primers and the use thereof for polymerase chain reaction (PCR) amplification of *Oxalobacter formigenes* nucleotide sequences. Amplified Oxalobacter sequences can then be detected using the polynucleotide probes of the subject invention.

BRIEF DESCRIPTION OF THE DRAWINGS

FIGS. 2A–2B show the nucleotide sequence of the formyl-CoA transferase gene and the deduced amino acid sequence of the formyl-CoA transferase polypeptide from *Oxalobacter formigenes*. Bolded letters represent amino acid residues determined by N-terminal protein sequencing.

FIGS. 3A–3B show the nucleotide sequence of the oxalyl-CoA decarboxylase gene and flanking regions from *Oxalobacter formigenes*. The consensus ribosome-binding site lies approximately 10 bases upstream (double-underlined letters) from the putative translation initiation codon (positions 1 to 3). A rho-independent termination sequence lies at positions 1758 to 1790 (double-underlined letters). A putative TPP-binding site appears between positions 1351 and 1437.

FIGS. 9A–9B show the identification of sequence homologies within the oxc gene expressed in representative group I and group II strains of *Oxalobacter formigenes* to design oligonucleotide probes. Partial sequences of 5'-end of the oxc gene generated by PRC amplification of the region bounded by the primer pair, AP34/AP21. A region of high homology shared by all strains (between bp 13 and 43) was selected for the genus-specific oligonucleotide probe, AP286, while regions of high homology shared by only group I strains (between bp 197 and 214) or shared only by group II strains (between bp 133 and 150) were selected for group-specific oligonucleotide probes, HS2 and AP307, respectively.

BRIEF DESCRIPTION OF THE SEQUENCES

Figure 1A:
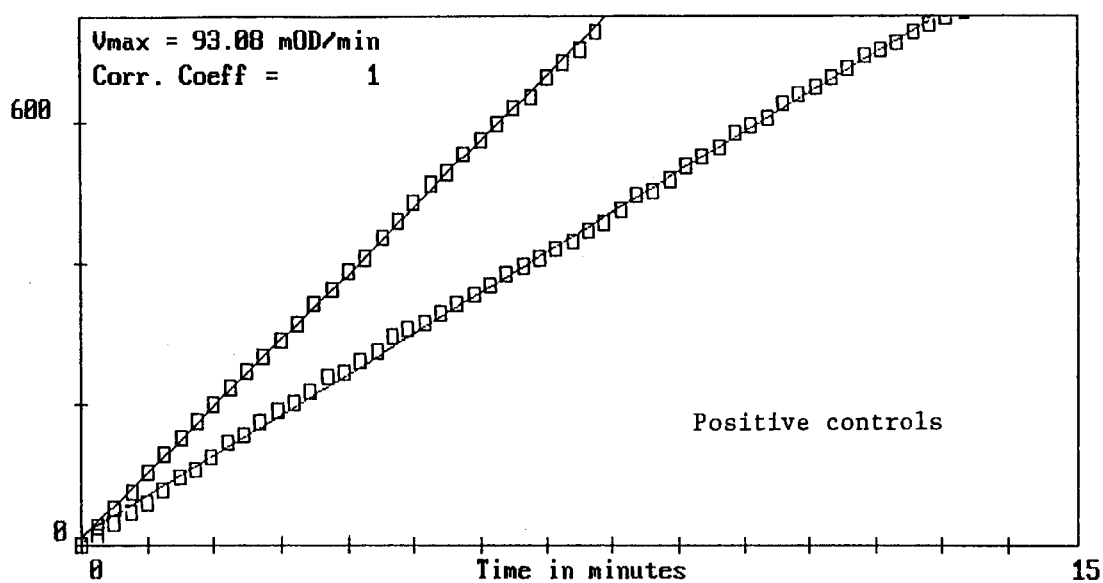
FIGS. 1A–1E show the detection of varying concentrations of oxalate in a sample. Colorimetric absorbance for each sample was plotted over time (minutes). Positive and negative control panels are also shown.
Figure 1B:
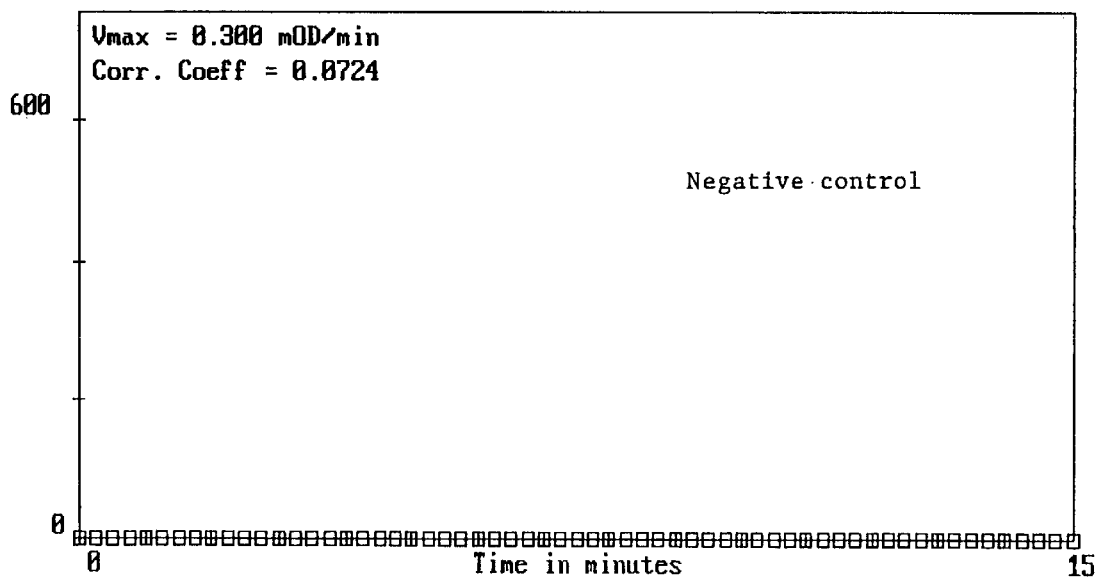
Figure 1C:
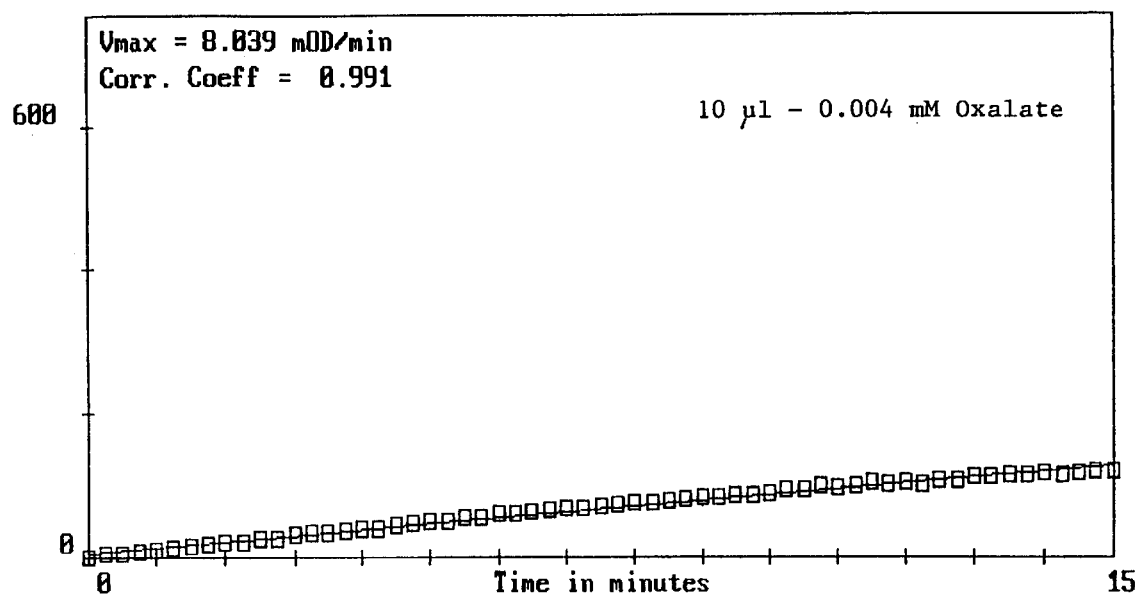
Figure 1D:
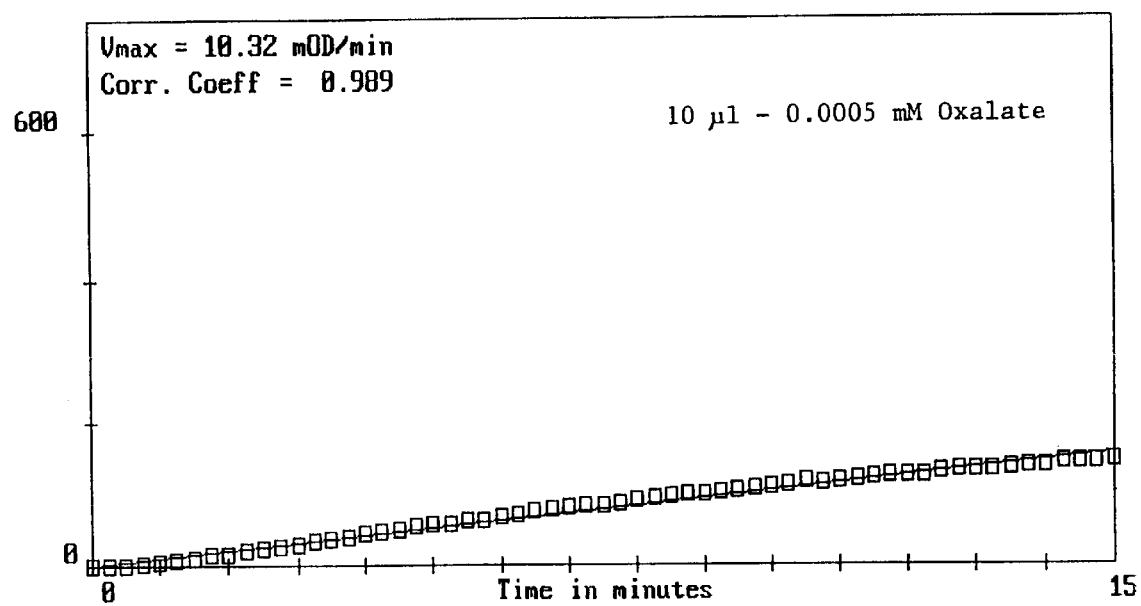
Figure 1E:
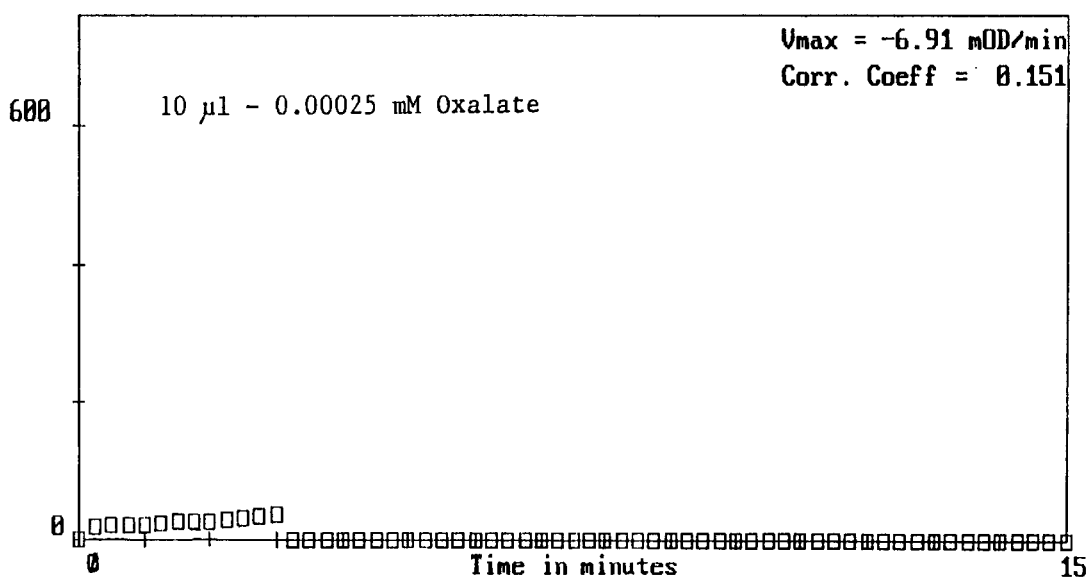
Figure 2A:
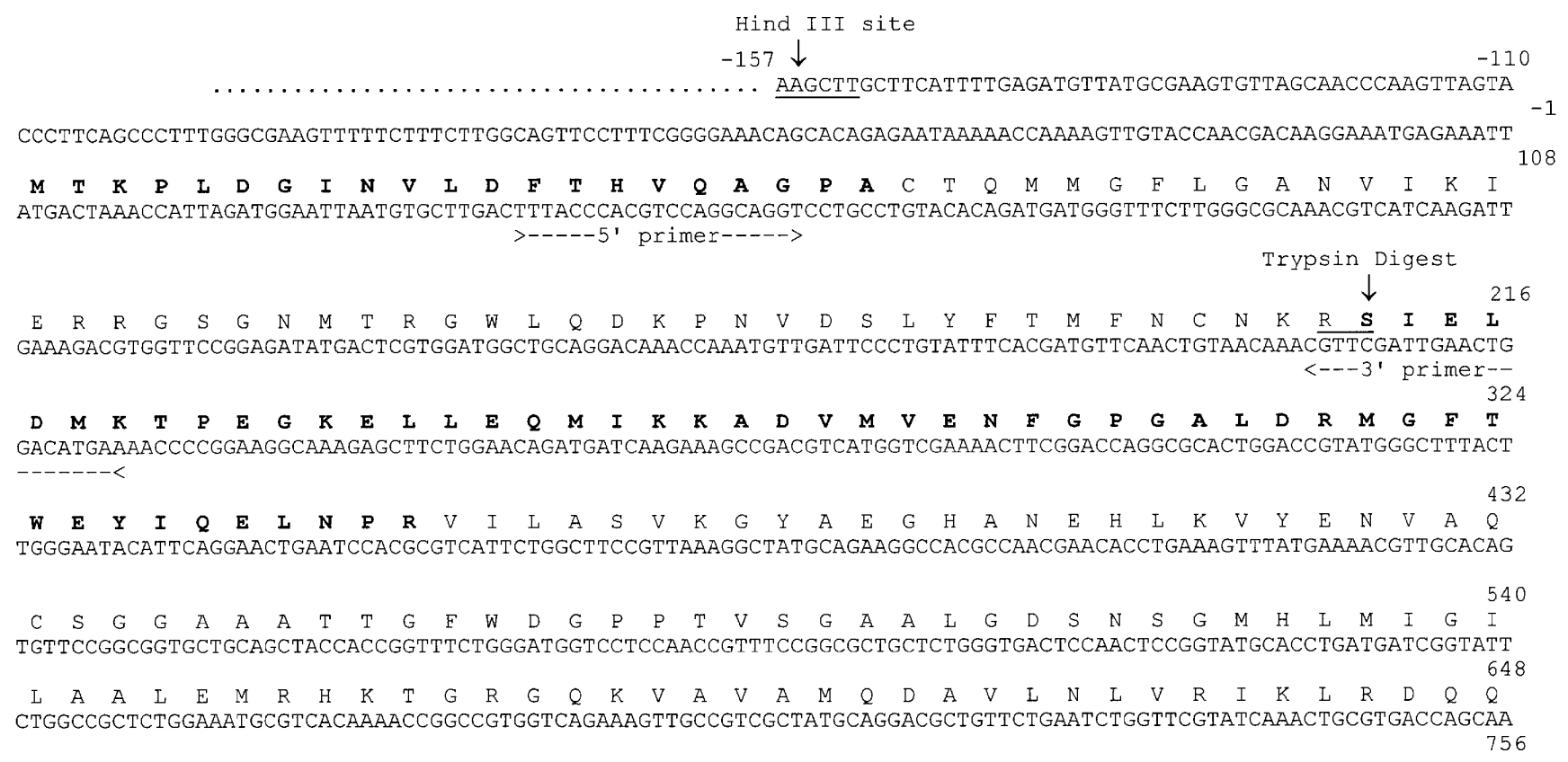

SEQ ID NO. 1 is a nucleotide sequence for the formyl-CoA transferase gene (also shown in FIG. 2).

SEQ ID NO. 2 is a polypeptide encoded by SEQ ID NO. 1, which can be used according to the subject invention.

SEQ ID NO. 3 is the nucleotide sequence for the oxalyl-CoA decarboxylase gene (also shown in FIG. 3).

SEQ ID NO. 4 is a polypeptide encoded by SEQ ID NO. 3, which can be used according to the subject invention.

SEQ ID NO. 5 is an oxalyl-CoA decarboxylase sequence, which can be used as a probe according to the subject invention.

SEQ ID NO. 6 is an oxalyl-CoA decarboxylase sequence, which can be used as a probe or PCR primer according to the subject invention.

SEQ ID NO. 7 is an oxalyl-CoA decarboxylase 5'-primer, which can be used according to the subject invention.

SEQ ID NO. 8 is an oxalyl-CoA decarboxylase 3'-primer, which can be used according to the subject invention.

SEQ ID NO. 9 is an oxalyl-CoA decarboxylase sequence, which can be used as a probe or primer according to the subject invention.

SEQ ID NO. 10 is a formyl-CoA transferase sequence, which can be used as a probe according to the subject invention.

SEQ ID NO. 11 is an oxalyl-CoA decarboxylase sequence, which can be used as a PCR primer according to the subject invention.

SEQ ID NO. 12 is an oxalyl-CoA decarboxylase sequence, which can be used as a PCR primer according to the subject invention.

SEQ ID NO. 13 is an oxalyl-CoA decarboxylase sequence, which can be used as a PCR primer according to the subject invention.

SEQ ID NO. 14 is an oxalyl-CoA decarboxylase sequence, which can be used as a probe according to the subject invention.

SEQ ID NO. 15 is an oxalyl-CoA decarboxylase sequence, which can be used as a probe according to the subject invention.

SEQ ID NO. 16 is an oxalyl-CoA decarboxylase sequence, which can be used as a probe according to the subject invention.

SEQ ID NO. 17 is an oxalyl-CoA decarboxylase sequence, which can be used as a PCR primer according to the subject invention.

SEQ ID NO. 18 is a formyl-CoA transferase sequence, which can be used as a PCR primer according to the subject invention.

SEQ ID NO. 19 is a formyl-CoA transferase sequence, which can be used as a PCR primer according to the subject invention.

DETAILED DESCRIPTION OF THE INVENTION

The subject invention provides an accurate, sensitive assay for oxalate in biological samples such as urine and serum. Elevated levels of oxalate are correlated with urinary tract stone formation, as well as other health problems. Early detection of high levels of oxalate makes it possible to prevent, delay or reduce adverse health consequences through appropriate medication and through modulation of diet.

In the presently described diagnostic system, two enzymes are used to catabolize oxalate to carbon dioxide and formate. Specifically, any oxalate that may be present in a sample being assayed is converted into formate and carbon dioxide ($CO_2$) through the combined action of the enzymes oxalyl-CoA decarboxylase and formyl-CoA transferase. The formate can then be detected using a variety of techniques known in the art. In a preferred embodiment, the production of formate is measured colorimetrically by linking the catabolism of formate with the production of a detectable color change (for example, the formation of a compound that absorbs a particular wavelength of light). The production of formate is directly correlated with the amount of oxalate present in the sample. Therefore, if a known amount of formate is produced using the subject enzyme system, then the amount of oxalate present in the sample can be easily quantitated.

In a preferred embodiment, the enzymes used in the subject invention are expressed by genes from the bacterium *Oxalobacter formigenes*. The genes encoding both oxalyl-CoA decarboxylase (Lung et al., 1994) and formyl-CoA transferase enzymes have been cloned and expressed, thus providing a readily-available source of reagent material. The subject assay is capable of detecting oxalate levels in a range as low as 0.00025–0.0005 mM (FIGS. 1A–1E). This level of sensitivity makes the subject assay capable of direct detection of oxalate in serum samples consisting of little as 10 µl volume. The described system can be easily automated with standard systems known in the art.

In a preferred embodiment of the subject assay, the enzymatic reaction can be carried out in the wells of flat-bottomed 96-well microtiter plates and read in an automated plate reader. Suitable concentrations of the assay reagents oxalyl-CoA decarboxylase, oxalyl-CoA, β-NAD, formate dehydrogenase, and the sample to be assayed are added to the microtiter wells. The reaction is then brought to equilibrium (two minute incubation at 37° C. in the plate reader) to permit degradation of any residual formate that may be present in the sample. The formyl-CoA transferase enzyme is then added to the mixture to start the reaction, and the plate is read at 15 second intervals. Formate production is determined by measuring the reduction in NAD in the presence of formate dehydrogenase by detecting changes in absorbance of the sample at 340 nm (Baetz and Allison, 1989). The quantity of oxalate is determined by comparison of the unknown samples with standards having a known amount of oxalate.

Further, the enzymatic reaction of the subject assay will not be initiated until the formyl-CoA transferase, oxalyl-CoA decarboxylase, and oxalyl-CoA are all present within the reaction mixture. Therefore, initiation of the enzymatic reaction can be prevented by withholding one of the above reagents from the reaction mix. Preferably, oxalyl-CoA decarboxylase and oxalyl-CoA are added first, and the reaction is initiated by the addition of formyl-CoA transferase to the mix. However, the order of addition of the three reagents is not material to the function of the assay, so long as one of the reagents is withheld until just prior to the desired initiation point of the assay.

The formyl-CoA transferase and oxalyl-CoA decarboxylase enzymes used in the subject invention can be obtained and purified as a natural product of *Oxalobacter formigenes* (Baetz and Allison, 1989 and 1990). Alternatively, the enzymes can be obtained from host cells expressing the recombinant polynucleotide molecules of the subject invention that encode the enzymes. Other reagents used in the subject assay can be obtained from conventional sources, such as Sigma Chemical Company, St. Louis, Mo. Further, a person of ordinary skill in the art can readily determine the optimal concentrations of the reagents to use in the assay described herein.

A further aspect of the subject invention concerns the cloning, sequencing and expression of the *Oxalobacter formigenes* gene which encodes the formyl-CoA transferase used in the assay that is a subject of the invention. The gene was cloned using degenerate oligonucleotide probes (based on partial amino acid sequencing of tryptic peptides) to screen an Oxalobacter genomic DNA library. The gene encodes a polypeptide having a molecular weight of approximately 40 kD. The subject invention further concerns the cloning, sequencing, and expression of the gene which encodes oxalyl-CoA decarboxylase from *Oxalobacter formigenes*. The nucleotide sequence of the cDNA of formyl-CoA transferase and oxalyl-CoA decarboxylase are shown in FIGS. 2A–2B and 3A–3B, respectively (SEQ ID NOS. 1 and 3).

Because of the redundancy of the genetic code, a variety of different polynucleotide sequences can encode the formyl-CoA transferase polypeptide disclosed herein. It is well within the skill of a person trained in the art to create alternative polynucleotide sequences encoding the same, or essentially the same, polypeptide of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional enzymatic activity of the encoded polypeptide. Further, the subject invention contemplates those polynucleotide molecules having sequences which are sufficiently homologous with the DNA sequences shown in FIGS. 2A–2B and 3A–3B (SEQ ID NOS. 1 and 3) so as to permit hybridization with those sequences under standard high-stringency conditions. Such hybridization conditions are conventional in the art (see, e.g., Maniatis et al., 1989).

As a person skilled in the art would appreciate, certain amino acid substitutions within the amino acid sequence of the polypeptide can be made without altering the functional activity of the enzyme. For example, amino acids may be placed in the following classes: non-polar, uncharged polar, basic, and acidic. Conservative substitutions, whereby an amino acid of one class is replaced with another amino acid of the same class, fall within the scope of the subject invention so long as the substitution does not materially alter the enzymatic reactivity of the polypeptide. Non-conservative substitutions are also contemplated as long as the substitution does not significantly alter the functional activity of the encoded polypeptide.

The polynucleotides of the subject invention can be used to express the recombinant formyl-CoA transferase enzyme. They can also be used as a probe to detect related enzymes. The polynucleotides can also be used as DNA sizing standards.

The polypeptides encoded by the polynucleotides can be used to raise an immunogenic response to the formyl-CoA transferase enzyme. They can also be used as molecular weight standards, or as inert protein in an assay. The polypeptides can also be used to detect the presence of antibodies immunoreactive with the enzyme.

The polynucleotide sequences of the subject invention may be composed of either RNA or DNA. More preferably, the polynucleotide sequences are composed of DNA. The subject invention also encompasses those polynucleotides that are complementary in sequence to the polynucleotide sequences disclosed herein.

Another aspect of the subject invention pertains to kits for carrying out the enzyme assay for oxalate. In one embodiment, the kit comprises, in packaged combination and in relative quantities to optimize the sensitivity of the described assay method, (a) the oxalyl-CoA decarboxylase, oxalyl-CoA, β-NAD, and formate dehydrogenase; and (b) formyl-CoA transferase. The kit may optionally include other reagents or solutions, such as buffering and stabilization agents, along with any other reagents that may be required for a particular signal generation system. Other reagents such as positive and negative controls can be included in the kit to provide for convenience and standardization of the assay method.

The subject invention further concerns a method for detecting the presence of *Oxalobacter formigenes* organisms in a sample. Specific polynucleotide probes can be prepared based on the nucleotide sequence of either the oxalyl-CoA decarboxylase or the formyl-CoA transferase gene sequence of *Oxalobacter formigenes*. The polynucleotide probes of the subject invention can be used to identify *Oxalobacter formigenes* in a sample, and to classify the strain of *Oxalobacter formigenes* detected. The polynucleotide probes of the subject invention can be used according to standard procedures and conditions to specifically and selectively detect polynucleotide sequences that have sufficient homology to hybridize with the probe. DNA can be isolated from bacterial microorganisms in a biological specimen (e.g., biopsy, fecal matter, tissue scrapings, etc.) using standard techniques known in the art and the isolated DNA screened for hybridization with Oxalobacter oxalyl-CoA decarboxylase-specific and/or formyl-CoA transferase-specific polynucleotide probes. Various degrees of stringency can be employed during the hybridization, depending on the amount of probe used for hybridization, the level of complementarity (i.e., homology) between the probe and target DNA fragment to be detected. The degree of stringency can be controlled by temperature, ionic strength, pH, and the presence of denaturing agents such as formamide during hybridization and washing. Hybridization methods and conditions are known in the art and are generally described in *Nucleic Acid Hybridization: A Practical Approach* (Hames, B. D., S. J. Higgins, eds.), IRL Press (1985).

The polynucleotide probes of the subject invention include, for example, the oxalyl-CoA decarboxylase probe A (SEQ ID NO. 5), probe AP15 (SEQ ID NO. 6), and probe AP34 (SEQ ID NO. 9), probe AP286 (SEQ ID NO. 14), probe AP307 (SEQ ID NO. 15), and probe HS-2 (SEQ ID NO. 16), specifically exemplified herein. Probes for formyl-CoA transferase include, for example, probe AP273 (SEQ ID NO.10) specifically exemplified herein. The nucleotide sequences of the exemplified probes are shown below:

```
Probe A      5'-GAGCGATACCGATTGGA-3'              (SEQ ID NO. 5)

Probe AP15   5'-GCACAATGCGACGACGA-3'              (SEQ ID NO. 6)

Probe AP34   5'-ATACTCGGAATTGACGT-3'              (SEQ ID NO. 9)

Probe AP273 5'-TTCATGTCCAGTTCAATCGAACG-3'         (SEQ ID NO. 10)

Probe AP286 5'-GACAATGTAGAGTTGACTGATGGCTTTCATG-3' (SEQ ID NO. 14)

Probe AP307 5'-CAGGATGGTCAGAAGTTC-3'              (SEQ ID NO. 15)

Probe HS-2   5'-CCGGTTACATCGAAGGA-3'              (SEQ ID NO. 16)
```

The polynucleotide probes contemplated in the subject invention also include any polynucleotide molecule comprising a nucleotide sequence capable of specifically hybridizing with oxalyl-CoA decarboxylase or formyl-CoA transferase polynucleotide sequence of the present invention. As used herein, reference to "substantial homology" or "substantially complementary" refers not only to polynucleotide probes of the subject invention having 100% homology with the nucleotide sequence of the target polynucleotide, or fragments thereof, but also to those sequences with sufficient homology to hybridize with the target polynucleotide. Preferably, the degree of homology will be 100%; however, the degree of homology required for detectable hybridization will vary in accordance with the level of stringency employed in the hybridization and washes. Thus, probes having less than 100% homology to the oxalyl-CoA decarboxylase or formyl-CoA transferase polynucleotide sequences can be used in the subject method under appropriate conditions of stringency. In a preferred embodiment, high stringency conditions are used. In addition, analogs of nucleosides may be substituted for naturally occurring nucleosides within the polynucleotide probes. Such probes having less than 100% homology or containing nucleoside analogs are within the scope of the subject invention. The skilled artisan, having the benefit of the disclosure contained herein, can readily prepare probes encompassed by the subject invention.

In addition, the subject invention also concerns polynucleotide primers that can be used for polymerase chain reaction (PCR) amplification of *Oxalobacter formigenes* nucleotide sequences. PCR amplification methods are well known in the art and are described in U.S. Pat. Nos. 4,683,195; 4,683,202; and 4,800,159. The polynucleotide primers and probes of the present invention can also be used to amplify nucleotide sequences encoding oxalyl-CoA decarboxylase and formyl-CoA transferase by non-PCR based amplification methods. The subject primers and probes in any method where amplification of specific sequences is desired. In a preferred embodiment, the polynucleotide primers are based on the oxalyl-CoA decarboxylase or formyl-CoA transferase gene sequence and can be used to amplify the full length or a portion of the target gene. The amplified Oxalobacter sequences can be detected using the probes of the subject invention according to standard procedures known in the art.

The polynucleotide primers of the subject invention include, for example, oxalyl-CoA decarboxylase PCR primer 1 (SEQ ID NO. 7), PCR primer 2 (SEQ ID NO. 8), PCR primer AP15 (SEQ ID NO. 6), PCR primer AP22 (SEQ ID NO. 11), PCR primer AP34 (SEQ ID NO. 9), PCR primer AP21 (SEQ ID NO. 17), OXF6 (SEQ ID NO. 12), and OXF7 (SEQ ID NO. 13), specifically exemplified herein. The nucleotide sequences of the exemplified PCR primers are shown below:

```
PCR primer 1      5'-CAGGTTATGCAGCTTCT-3'    (SEQ ID NO. 7)

PCR primer 2      5'-GGATGGTTGTCAGGCAG-3'    (SEQ ID NO. 8)

PCR primer AP15   5'-GCACAATGCGACGACGA-3'    (SEQ ID NO. 6)

PCR primer AP22   5'-GTAGTTCATCATTCCGG-3'    (SEQ ID NO. 11)

PCR primer AP34   5'-ATACTCGGAATTGACGT-3'    (SEQ ID NO. 9)

PCR primer AP21   5'-TCCAATCGGTATCGCTC-3'    (SEQ ID NO. 17)

OXF6              5'-AATGTAGAGTTGACTGA-3'    (SEQ ID NO. 12)

OXF7              5'-TTGATGCTGTTGATACG-3'    (SEQ ID NO. 13)
```

The primer pair AP34 and AP21 (derived from oxc sequences between bp −59 to −41 and by 451 to 435, respectively), consistently amplifies a 500 bp segment of oxc from all *O. formigenes* strains and isolates tested. PCR application of whole fecal DNA with this genus-specific primer pair, in conjunction with Southern Blotting using genus and group specific probes, now provides a rapid diagnostic tool to detect and speciate *O. formigenes*. Time-consuming steps, e.g., agarose-gel electrophoresis and Southern blot hybridizations, can be substituted with newer technologies such as microtiter-plate based colorimetric or fluorogenic assays (Jordan et al., 1996).

Polynucleotide primers contemplated by the subject invention also include any polynucleotide molecule comprising a nucleotide sequence capable of specifically priming amplification of oxalyl-CoA decarboxylase or formyl-CoA transferase polynucleotide sequences disclosed herein. As used herein, reference to "substantial homology" or "substantially complementary" refers not only to polynucleotide primers of the subject invention having 100% homology with the nucleotide sequence of the target polynucleotide, or fragments thereof, but also to those sequences with sufficient homology to hybridize with and prime the amplification of a target polynucleotide. Preferably, the degree of homology will be equal to or about 100%. The skilled artisan, having the benefit of the disclosure contained herein, can readily prepare other primers of varying nucleotide length and sequence that can be used to amplify all or portions of the oxalyl-CoA decarboxylase and/or the formyl-CoA transferase gene.

The polynucleotide probes and primers of the subject invention can be chemically synthesized or prepared through recombinant means using standard methods and equipment. The polynucleotide probes and primers can be in either single- or double-stranded form. If the probe or primer is double-stranded, then single-stranded forms can be prepared from the double-stranded form. The polynucleotide probes and primers may be comprised of natural nucleotide bases or known analogs of the natural nucleotide bases. The probes and primers of the subject invention may also comprise nucleotides that have been modified to bind labeling moieties for detecting the probe or primer or amplified gene fragment.

The polynucleotide molecules of the subject invention can be labeled using methods that are known in the art. The polynucleotides may be radioactively labeled with an isotope such as $^3H$, $^{35}S$, $^{14}C$, or $^{32}p$. The polynucleotides can also be labeled with fluorophores, chemiluminescent compounds, or enzymes. For example, a polynucleotide molecule could be conjugated with fluorescein or rhodamine, or luciferin or luminol. Similarly, the polynucleotide molecule can be conjugated with an enzyme such as horseradish peroxidase or alkaline phosphatase. Polynucleotide molecules can also be detected by indirect means. For example, the polynucleotide may be conjugated with ligands, haptens, or antigenic determinants. The conjugated polynucleotide is then contacted with the ligand receptor, with an anti-ligand molecule that binds to the ligands, or with an antibody that binds to the hapten/antigenic determinant, respectively. For example, the polynucleotide can be labeled with digoxygenin and detected with labeled anti-digoxygenin antibodies. The ligand receptor, anti-ligand molecule, or antibody may be directly labeled with a detectable signal system, such as a fluorophore, chemiluminescent molecule, radioisotope, or enzyme. Methods for preparing and detecting labeled moieties are known in the art.

The subject invention also concerns methods for quantitatively detecting oxalyl-CoA decarboxylase and formyl-CoA transferase nucleotide sequences and, thereby, determining the number of *Oxalobacter formigenes* in a sample. General methods and techniques for performing quantitative PCR are known in the art (Tarmuzzer el al., 1996).

In one embodiment of the present detection method, samples to be tested for the presence of *Oxalobacter formigenes* are obtained from a person or animal, and DNA is isolated from the specimen using standard techniques known in the art. For example, cells can be lysed in an alkali solution, the nucleic acid extracted in phenol:chloroform, and then precipitated with ethanol. The DNA is then fragmented into various sizes using restriction endonuclease enzymes or other means known in the art. The DNA fragments are then electrophoretically separated by size on an agarose gel. In an alternative embodiment, the DNA fragments are subjected to PCR amplification using PCR primers of the present invention prior to gel electrophoresis in order to specifically amplify portions of the formyl-CoA transferase and oxalyl-CoA decarboxylase genes.

After the DNA fragments are separated on the gel, the size-fractionated DNA fragments are transferred to a membrane matrix, such as nitrocellulose, nylon, or polyvinylidene difluoride (PVDF), by Southern blotting. The DNA immobilized on the membrane matrix is single-stranded. Polynucleotide probes of the subject invention are then contacted with the membrane and allowed to hybridize with the DNA immobilized on the membrane. A probe of the present invention can be labeled with a detectable signal, such as a radioisotope, or the probe can be labeled with a hapten or antigen such as digoxigenin. The hybridization can be performed under conditions known in the art. After hybridization of the probe with the DNA fragments on the membrane, the membrane is washed to remove non-hybridized probe. Standard wash conditions are known in the art, and the stringency and number of washes employed can vary.

The membrane is then tested or observed for the presence of hybridized probe. For example, if the hybridized probe was labeled with a hapten or antigen, then it can be detected using an antibody that binds to the conjugated hapten or antigen on the probe. The antibody can be directly labeled with a detectable fluorophore, chemiluminescent molecule, radioisotope, enzyme, or other signal generating system known in the art. Alternatively, the antibody can be detected using a secondary reagent that binds to the antibody, such as anti-immunoglobulin, protein A, protein G, and other antibody binding compositions known in the art. The secondary reagent can be labeled with a detectable fluorophore, chemiluminescent molecule, radioisotope, or enzyme. The presence of a detectable hybridization signal on the membrane indicates the presence of *Oxalobacter formigenes* in a test sample.

The subject invention also concerns a kit for the detection of *Oxalobacter formigenes* in a sample. A kit contemplated by the subject invention may include in one or more containers: polynucleotide probes, positive and negative control reagents, and reagents for detecting the probes. The kit may also include polynucleotide primers for performing PCR amplification of specific *Oxalobacter formigenes* genes. In a preferred embodiment, the polynucleotide probes and primers are specific for the oxalyl-CoA decarboxylase and formyl-CoA transferase genes of *O. formigenes*.

The subject invention also concerns a dipstick device comprising the enzymes of the subject invention and dyes and/or substrates immobilized on a carrier matrix. Any dye or substrate that yields a detectable product upon exposure to the reaction products that are produced by the enzymatic reaction of oxalate with oxalyl-CoA decarboxylase and formyl-CoA transferase as described herein is contemplated for use with the subject dipstick device. The carrier matrix of the assay device can be composed of any substance capable of being impregnated with the enzyme and dye components of the subject invention, as long as the matrix is substantially inert with respect to the analyte being assayed for. For example, the carrier matrix may be composed of paper, nitrocellulose, PVDF, or plastic materials and the like.

Incorporation of the enzymes, dye and other components on the carrier matrix can be accomplished by any method such as dipping, spreading or spraying. A preferred method is impregnation of the carrier matrix material by dipping in a reagent solution and drying to remove solvent. Drying can be accomplished by any means which will not deleteriously affect the reagents incorporated, and typically is by means of an air drying oven.

The dipstick device of the subject invention is dipped in or contacted with a sample to be tested for the presence or amount of oxalate. Positive and negative controls can be used in conjunction with the dipstick device. An appropriate amount of time is allowed to pass and then the dipstick is assessed for a positive reaction by visual inspection. If oxalate is present in the sample then a detectable signal, usually in the form of a color, can be observed on the dipstick. Typically, the intensity of the color developed in a fixed time period is proportional to the concentration of oxalate present in the sample.

All publications cited herein are incorporated reference.

Following are examples which illustrate procedures, including the best mode, for practicing the invention. These examples should not be construed as limiting. All percentages are by weight and all solvent mixture proportions are by volume unless otherwise noted.

EXAMPLE 1

Determination of Level of Sensitivity of Enzyme Assay System

Samples containing oxalate at concentrations ranging from 0.004 mM to 0.00025 mM were prepared in 10 µl volumes. The samples were then assayed using the enzyme system of the subject invention in 96-well microtiter plates. Reagents were then added at the following concentrations: $KH_2PO_4$ (pH 6.7), 50 mM; $MgCl_2$, 5 mM; thiamine PPi (TPP), 2 mM; oxalyl-CoA, 0.375 mM; β-NAD, 1.0 mM; formate dehydrogenase, 0.25 IU; and oxalyl-CoA decarboxylase, 0.03 U. The reaction mixture was then incubated at 37° C. for 2 minutes in order to permit the degradation of any residual formate that may be present in the sample mixture. The reaction was then initiated by the addition of formyl-CoA transferase to the sample mixture. Changes in A340 were measured every 15 seconds at 37° C. (FIGS. 1A–1E). Appropriate positive and negative controls were run simultaneously with the assay.

EXAMPLE 2

Detection of *Oxalobacter formigenes* in a Sample

Strains of *Oxalobacter formigenes* used in the following methods are listed in Table 1 below.

TABLE 1

Description of the *Oxalobacter formigenes* strains

| Group Classification of *O. formigenes* strains[a] | Strain | Source of Isolate |
|---|---|---|
| Group I | OxB | Sheep rumen |
| | OxWR | Wild rat cecum |
| | SOx-4 | Freshwater lake sediment |
| | SOx-6 | Freshwater lake sediment |
| | POxC | Pig cecum |
| | HC-1 | Human feces |
| Group II | BA-1 | Human feces |
| | OxK | Human feces |
| | HOxBLS | Human feces |
| | HOxRW | Human feces |
| | OxCR | Lab rat cecum |
| | OxGP | Guinea pig cecum |

[a]From Jensen and Allison (1994).

All *Oxalobacter formigenes* strains were grown in medium B containing 30 mM oxalate, as described in Allison et al. (1985). Human fecal samples (approximately 60 mg) were inoculated anaerobically into vials containing 9 ml of media B, then sequentially transferred through $10^{-8}$ dilutions. Cultures were incubated at 37° C. for 10 days and biochemically tested for the catabolic consumption of oxalate by $CaCl_2$ precipitation (50 µl media, 100 µl 1% $CaCl_2$, and 2.7 ml $dH_2O$) and spectrophotometric analyses (600 nm).

Cultures (10–15 ml) of *O. formigenes* were centrifuged at 10,000×g, the bacterial pellet was resuspended in 567 µl TE buffer (10 mM Tris-Cl, pH 7.5 plus 1 mM EDTA, pH 8.0), 30 µl 10% sodium dodecyl sulfate (SDS) and 3 µl of proteinase K (20 mg/ml), and the mixture incubated 5 hr at 37° C. to ensure bacterial cell lysis. Nucleic acids were extracted from the lysates using phenol/chloroform/isoamylalcohol (25:24:1). Chromosomal DNA was precipitated from the aqueous phase by adding ½ volume of 7.5 M ammonium acetate and 2 volumes of 100% ethanol. DNA was recovered by centrifugation (12,000×g), washed once with 70% ethanol, and the pellet resuspended in 15–20 µl $H_2O$. Bacterial DNA was also isolated directly from fresh human stool samples following lysis with chaotropic salt and guanidine thiocyanate, then binding to glass matrix (GlasPac, National Scientific Supply, San Rafael, Calif.) (Stacy-Phips et al., 1995).

Bacterial DNA was digested with the restriction endonuclease Hind III (Life Technologies, Inc., Gaithersburg, Md.). The restriction-enzyme generated fragments were size separated by gel electrophoresis through 0.5% agarose, stained with ethidium bromide (EtBr), illuminated with UV light, and photographed to document proper digestion. Digested DNA was then transferred from the agarose gels to positively-charged nylon membranes (Boehringer-Mannheim GmBH, Indianapolis, Ind.) by positive pressure blotting and UV cross-linking (Stratagene, LaJolla, Calif.). Hybridizations were carried out using internal sequence oligonucleotide probes. Oligonucleotides were synthesized in the University of Florida ICBR Oligonucleotide Synthesis Laboratory (Gainesville, Fla.) and have the sequences:

```
                                          (SEQ ID NO. 6)
AP15    5'-GCACAATGCGACGACGA-3'

(SEQ ID NO. 11)
AP22    5'-GTAGTTCATCATTCCGG-3'
```

-continued

AP34    5'-ATACTCGGAATTGACGT-3'  (SEQ ID NO. 9)

AP273   5'-TTCATGTCCAGTTCAATCGAACG-3'  (SEQ ID NO. 10).

Each oligonucleotide was end-labeled with digoxigenin in a reaction using terminal transferase. The digoxigenin-labeled oligonucleotide probes were hybridized to the immobilized DNA fragments and hybridization detected calorimetrically by enzyme-linked immunoassay (ELISA) using an anti-digoxigenin alkaline phosphatase conjugate according to the manufacturer's protocol provided with the GENIUS III detection system (Boehringer-Mannheim).

All PCRs were performed according to protocols described in Anderson et al. (1993). Briefly, 50 µl reactions contained 1.5 mM $MgCl_2$, 200 µM dNTP, 1.25 U Taq polymerase (GIBCO-BRL, Bethesda, Md.), 1 µg template DNA and 1 µM each of a 5' and 3' primer. A preferred reaction profile proved to be 94° C. for 5 min, then 45 cycles of 94° C. for 1 min of denaturation, 55° C. for 2 min of annealing and 72° C. for 3 min of primer extension. PCR products were size separated by gel electrophoresis in 1.2% agarose containing EtBr and photographed in UV light. PCR primer AP15 (SEQ ID NO. 6) and primer AP22 (SEQ ID NO. 11) were used as primers.

Figure 4:
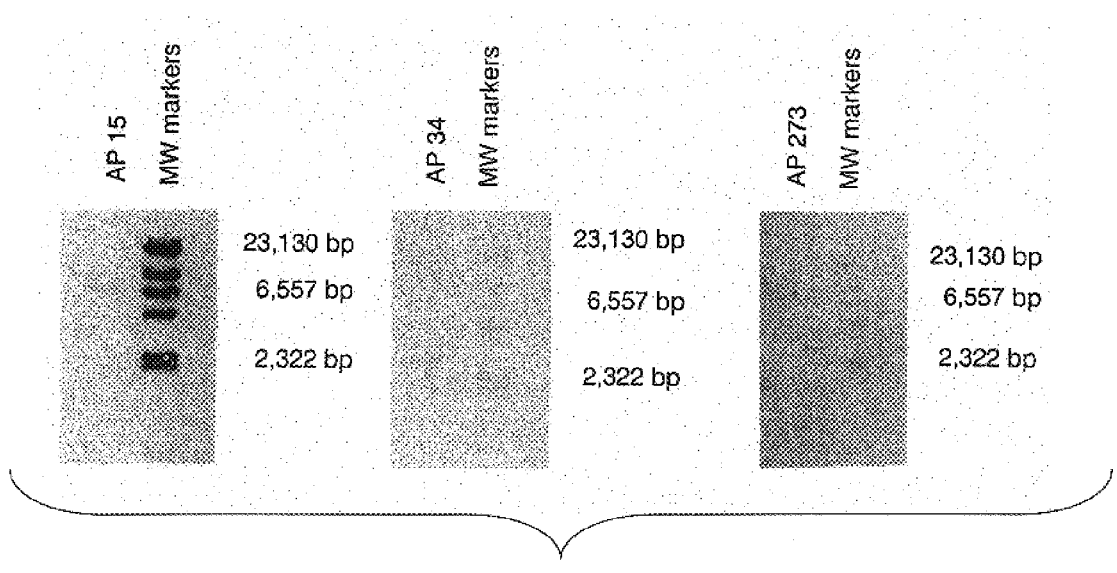
FIG. 4 shows an RFLP analysis of *O. formigenes*, strain OxB using probes specific for the oxc gene encoding oxalyl-CoA decarboxylase and the frc gene encoding formyl-CoA transferase. Genomic DNA isolated from a 14 day culture of *O. formigenes* strain OxB was digested with the restriction enzyme HIND III. The digested DNA was size fractionated by electrophoreses through 0.5% agarose gels, electroblotted to a nylon membrane, then hybridized with either probe AP15 (SEQ ID NO. 6) or probe AP34 (SEQ ID NO. 9) to detect oxc or probe AP273 (SEQ ID NO. 10) to detect frc.

Previous studies by Lung et al. (1994) showed that genomic DNA of *O. formigenes*, strain OxB, could be digested with the restriction enzyme Hind III and that a limited number of enzyme cleavage sites existed near or within the oxalyl-CoA decarboxylase (oxc) gene. A RFLP analysis of Hind III digested OxB genomic DNA using either probe AP15 (SEQ ID NO. 6), a probe homologous to an internal sequence of the oxc gene, probe AP34 (SEQ ID NO. 9), a probe homologous to a 5'-end sequence of the oxc gene but separated from the probe AP15 (SEQ ID NO. 6) sequence by a Hind III site, or probe AP273 (SEQ ID NO. 10), a probe homologous to an internal sequence of the formyl-CoA transferase (frc) gene, is shown in FIG. 4. Using probe AP15 (SEQ ID NO. 6), a fragment of approximately 7 kb containing a portion of the oxc gene was detected, while fragments of approximately 3 kb were detected using either probe AP34 (SEQ ID NO. 9) or probe AP273 (SEQ ID NO. 10). The 3 kb fragment identified by probe AP34 (SEQ ID NO. 9) is distinct from the 3 kb fragment detected by probe AP273 (SEQ ID NO. 10).

Figure 5:
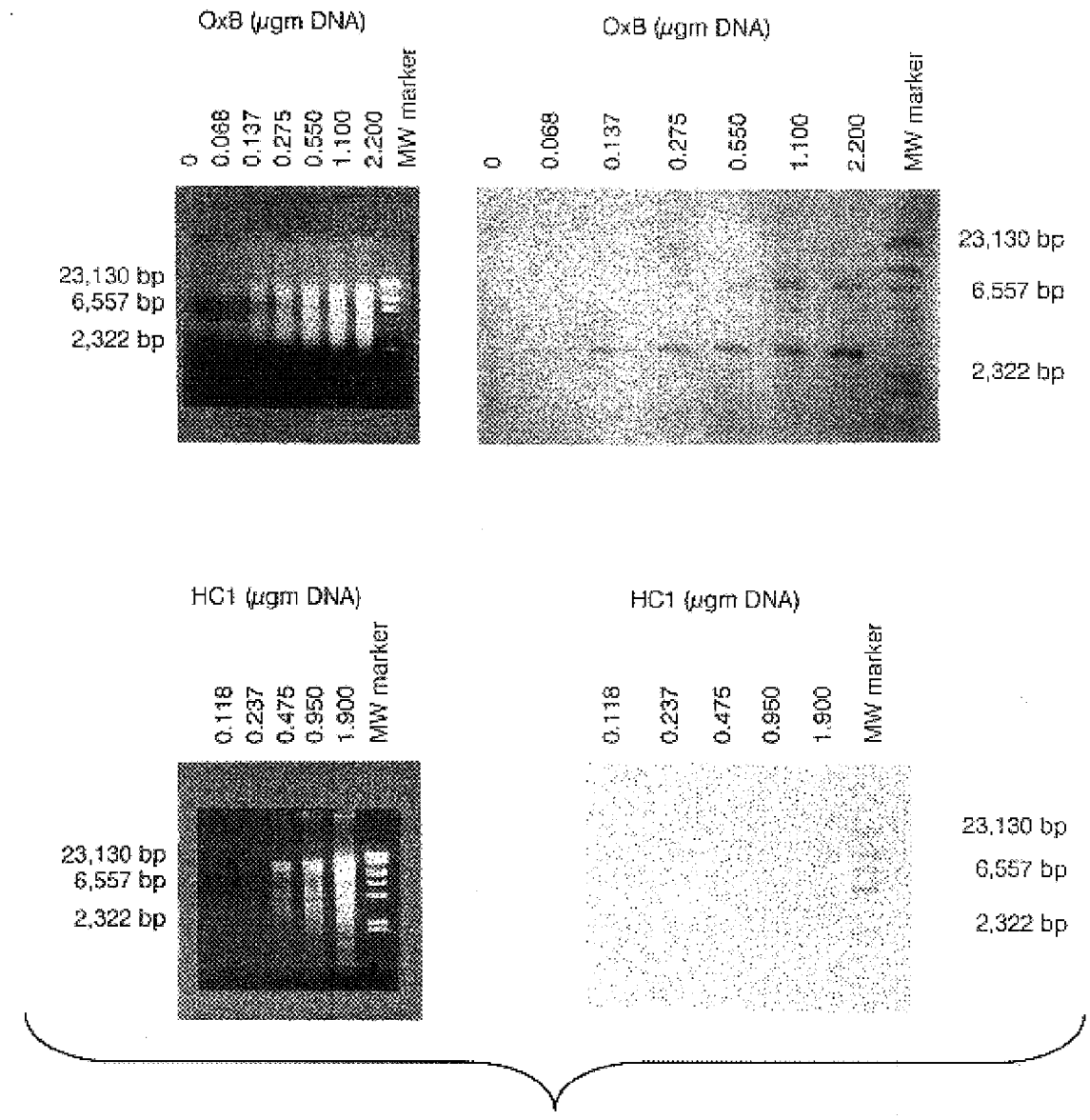
FIG. 5 shows the sensitivity of detecting the oxc and frc genes in RFLP of *O. formigenes* strain OxB versus strain HC-1. Genomic DNA from each of the two strains was digested with the restriction enzyme HIND III. Two-fold serial dilutions were made of the digested DNA and size fractionated by electrophoresis through 0.5% agarose gels (left panels). RFLP analyses were carried out as described in FIG. 4, except the nylon membranes were hybridized with a 1:1 mixture of probe AP15 (SEQ ID NO. 6) plus probe AP273 (SEQ ID NO. 10) (right panels).

As shown in FIG. 5, the oxalyl-CoA decarboxylase and formyl-CoA transferase genes were consistently detected in samples containing as little as 0.06 to 0.20 µg of *O. formigenes*, strain OxB, DNA or approximately 0.20 to 0.40 µg of *O. formigenes* DNA from other group I strains, such as HC-1. The 23-bp probe AP273 (SEQ ID NO. 10) can detect the frc gene in DNA samples containing only one-fourth the amount of DNA required for the 13 bp probe AP15 (SEQ ID NO. 6) to detect the oxc gene (FIG. 5, upper panel). These probes are highly specific for *O. formigenes* since they fail to bind to other bacterial DNA, including *Escherichia coli*, *Alcaligenes oxalaticus*, and *fecal bacteroides*.

Figure 6:
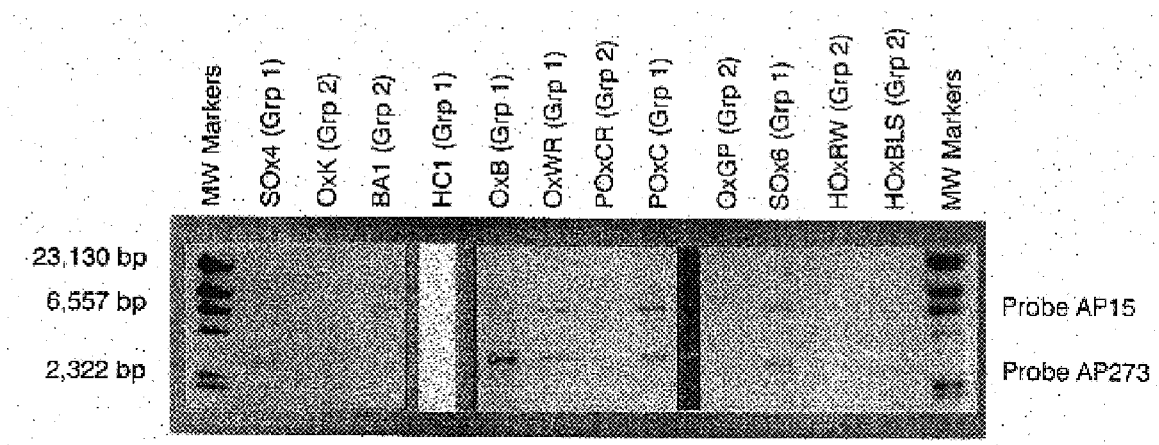
FIG. 6 shows the detection of the oxc and frc genes in various strains of *O. formigenes* by RFLP analysis. RFLP was carried out as described in FIG. 5.

Protein, lipid and genetic studies of several isolates of *O. formigenes* have provided the basis for dividing this genus into two major subgroupings (Jensen et al., 1994). When RFLP analyses were performed on genomic DNA isolated from various *Oxalobacter formigenes* strains, probes AP15 (SEQ ID NO. 6) and AP273 (SEQ ID NO. 10) were able to distinguish group I strains from group II strains on the Southern blot hybridizations (FIG. 6). All strains of *O. formigenes* belonging to group I (to which OxB is assigned) hybridized with both probe AP15 (SEQ ID NO. 6) and probe AP273 (SEQ ID NO. 10). Due to a characteristic slow growth of strain HC-1, only faint bands appeared in this experiment. In contrast, none of the *O. formigenes* strains assigned to group II hybridized with probe AP273 (SEQ ID NO.10) and only BA-1 hybridized with probe AP15 (SEQ ID NO.6). These data indicate a highly conserved homology of oxc and frc within group I strains and a less conserved homology within group II strains.

Figure 7:
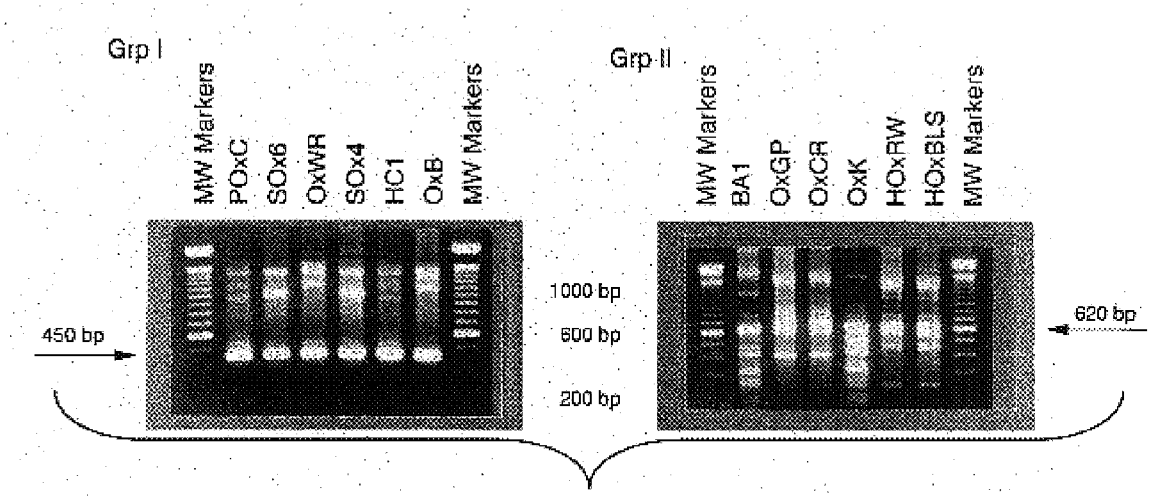
FIG. 7 shows PCR-based amplification of a genetic region of the oxc gene in various strains of *O. formigenes*. Using PCR primer AP15 (SEQ ID NO. 6) and primer AP22 (SEQ ID NO. 11) as PCR primers, PCR amplification was performed using genomic DNA isolated from each of the 12 strains of *O. formigenes* listed in Table 1 as template. PCR products were size fractionated by electrophoresis through 1.2% agarose gels and observed visually using ethidium bromide (EtBr) and UV light.

To increase the sensitivity of detecting *O. formigenes*, PCR was used to amplify that portion of oxc which by RFLP appeared to differentiate the group I and group II strains. Using primer AP15 (SEQ ID NO.6) and primer AP22 (SEQ ID NO.11) as PCR primers to amplify a DNA segment in the carboxy-terminal region of oxc, strains assigned to group I (i.e., OxB, HC-1, OxWR, POxC, SOx-4 and SOx-6) exhibited a common band at 452 bp (FIG. 7). In contrast, the other six strains, all belonging to group II, showed variable amplification patterns, but all showed a dominant PCR band of approximately 630 bp, with a weaker 452 bp band. Sequence analysis of this 630 bp band from strain OxK has revealed the presence of the 452 bp sequence present in the 630 bp PCR product. Close analysis of the group II strains suggest that their PCR amplification profiles are highly reproducible, suggesting group II strains may fall into three (sub)groupings: HOxBLS and HOxRW (subgroup 1), OxCR and OxGP (subgroup 2), and BA-1 and OxK (subgroup 3).

The use of PCR-based detection of the oxc gene to identify *O. formigenes* in clinical specimens was examined by comparing PCR and biochemical methods of detection. Specimen 1, known to be positive for *O. formigenes*, gave ambiguous results in biochemical testing for oxalate depletion, but exhibited the presence of the 450 bp PCR product indicative of an *O. formigenes* group I strain. Specimen 2, known to be negative for *O. formigenes*, proved negative using both PCR-based and biochemical testing. Specimen 3, known to be positive for *O. formigenes*, showed depletion of oxalate in all dilutions and revealed a PCR pattern suggestive of an *O. formigenes* group II strain. PCR amplification was not observed in the original culture or the first dilution due to the presence of inhibitors of PCR e.g., bile salts, bilirubin, etc.) which copurify with DNA.

Figure 8:
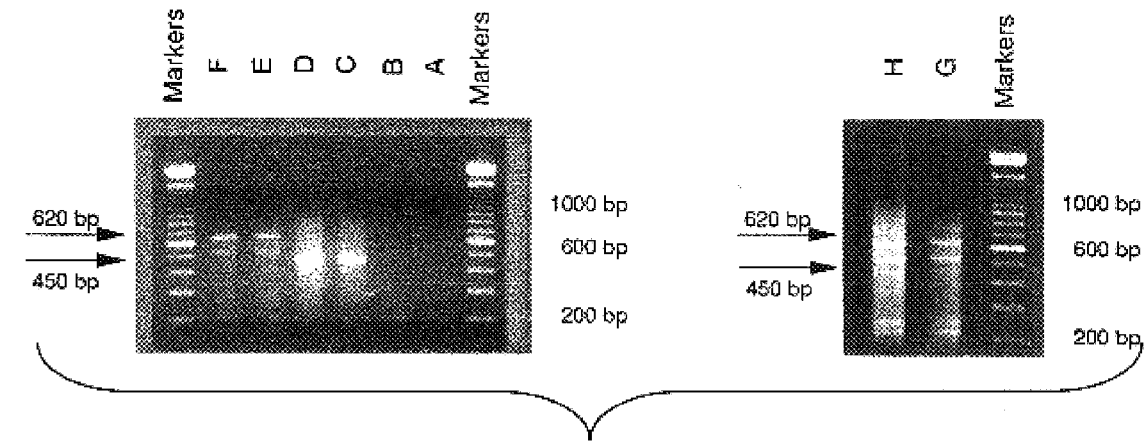
FIG. 8 shows a direct analysis of fecal samples for *O. formigenes*. Oxalobacter negative stool sample (A & B) was spiked with $10^2$ (C) and $10^4$ (D) cfu of OxB or $10^3$ (E) and $10^4$ (F) cfu of OxK per 0.1 gm. DNA from an unspiked *O. formigenes*-positive stool sample diluted 1:25 (G) and 1:50 (H).

To circumvent the inhibition of the PCR by factors co-purifying with the bacterial DNA, DNA isolation was performed by lysing fresh stool samples with guanidine thiocyanate followed by adsorption to and elution from glass matrices. Using this method, PCR-based detection of *O. formigenes* can be performed using fecal DNA diluted only 1:25 to 1:50 to eliminate PCR inhibitors. Sensitivity experiments using different stool samples spiked with strains OxB or OxK in the range of $10^1$ to $10^7$ cfu per 0.1 g of sample showed that as few as $10^2$ to $10^3$ cfu of *O. formigenes* per 0.1 g sample could be detected (FIG. 8). Again, PCR-based analyses of DNA isolated directly from a stool sample known to be positive for *O. formigenes* by culture methods, showed amplification patterns indicative of a group II strain (FIG. 8, lanes F & G).

EXAMPLE 3

Detection and Classification of *Oxalobacter formigenes* Bacterial Strains

*O. formigenes* strains used included OxB (isolated from sheep rumen) and HCl, OxK, BA1, HOxBLS, HOxRW, HOxRA, HOxCC13, and HOxHM8 (isolated from human feces). In addition, several new purified cultures, including HOxUK5, HOxUK88, HOxUK90, and HOxHS (grown from human feces), were also used. All strains and isolates were grown in media B containing 30 mM potassium oxalate, as described elsewhere (Allison et al., 1985), and maintained under strict anaerobic conditions until used.

Preparation of Genomic DNA from O. formigenes Cultures

Fifteen ml cultures of O. formigenes were centrifuged at 10,000×g, the bacterial pellet resuspended in 567 µl of TE buffer (10 mM Tris-HCl, pH 7.5, plus 1 mM EDTA, pH 8.0), 30 µl of 10% sodium dodecyl sulfate plus 3 µl of proteinase K (20 mg/ml), and this mixture incubated for 5 hours at 37° C. to ensure bacterial cell lysis. Nucleic acids were extracted from the lysates with phenol:chloroform:isoamyl alcohol (25:24:1). Chromosomal DNA was precipitated by adding ½ volume of 7.5 M ammonium acetate and 2 volumes of 100% ethanol. DNA was recovered by centrifugation (12,000×g) and washed once in 70% ethanol. The final DNA precipitation was resuspended in 20 µl $H_2O$.

Sequence Analysis of the oxc Genes

The primer pair, 5'-ATACTCGGAATTGACGT-3'(a 5'-primer designated AP34) (SEQ ID NO. 9) and 5'-TCCAATCGGTATCGCTC-3'(a 3'-primer designated AP21) (SEQ ID NO. 17) homologous to sequences within the 5'-end of the oxc gene present in strain OxB (Lung et al., 1994), was used to amplify a 500 bp DNA fragment from genomic DNA isolated from each of twelve human O. formigenes strains. Amplifications were performed in 50 µl PCR reactions containing 1.5 mM $MgCl_2$, 200 µM deoxynucleoside triphosphate, 1.25 U of Taq polymerase (Gibco-BRL, Bethesda, Md.), 1 µg of genomic DNA and 1 µM each of 5'- and 3'-primer. PCR were carried out for 35 cycles and included an initial 5 minute denaturation step at 94° C., 1 minute annealing (with a temperature stepdown from 60° C. to 55° C.), 1 minute extension at 72° C. and a final 8 minute extension at 72° C. The PCR products were size fractionated by electrophoreses through 1.2% agarose gels containing ethidium bromide for visualization of the bands in UV light. Each 500 bp PCR product was cloned into the TA cloning system, pCR-2.1 (Invitrogen, Inc., San Diego, Calif.). Competent DH5α E. coli bacteria were transfected with the recombinant plasmid and transformed bacteria selected on LB agar plates containing 10 µl/ml of ampicillin and 20 mg/ml of X-Gal. DNA from appropriate clones was isolated, checked for the presence of an insert of correct size by digestion with the restriction enzyme, Eco RI. Inserts of recombinant plasmids were sequenced using M13-forward and M13-reverse primers.

Clinical Samples

Fecal samples of 100 generally healthy children of either sex ranging in age from 0 to 12 years were examined for the presence of O. formigenes. All fecal samples were collected in Dzerzhinsk, a city in the Donetsk region of the Ukraine. This particular population was selected due to the fact that these children have had limited use of antibiotics, that might influence bacterial colonization of the intestinal tract, in treatment of childhood diseases. Approximately 25 mg sample of fresh stool (within 3–4 hours of collection), was inoculated into vials containing 10 ml of anaerobically sealed media B supplemented to 30 mM with potassium-oxalate. The vials were analyzed at the University of Florida, Gainesville, Fla. After incubation at 37° C. for one week, the loss of oxalate from each fecal culture was determined using a calcium-chloride precipitation method in which 50 µl culture media is mixed with 100 µl 0.1% $CaCl_2$ plus 3.0 ml $dH_2O$ and the absorbance of each mixture determined spectrophotometrically (600 nm). The calcium precipitation test for loss of oxalate has been repeatedly verified as reliable by other methods (e.g., gas chromatography and butyl esters) for detection of oxalate. Typically, cultures not showing catabolism of oxalate generally have O.D. readings of about 0.1, whereas cultures with oxalate degradation have O.D. readings less than about 0.02.

PCR-based Detection and Identification of O. formigenes

DNA was isolated from individual fecal cultures by the method of Phipps et al. (Stacy-Phipps et al., 1995) using guanidine thiocyanate as a chaotropic agent and glass-matrix for DNA binding. One µl of each DNA sample was used as template in a 50 µl PCR reaction as described above. The amplified PCR products were size separated by electrophoresis through 1.2% agarose gels containing ethidium bromide and visualized with UV light. Each reaction was controlled using a reaction containing all the components of the PCR with the exception of template DNA.

Southern Blot Analysis

Southern blots were carried out as previously detailed in Example 2. Briefly, the size separated PCR products were transferred to positively charged nylon membranes (Boehringer Mannheim GmBH, Indianapolis, Ind.) by positive pressure blotting and UV-crosslinking. The oxc derived genus specific (AP286), group I specific (HS-2) and group II specific (AP307) oligonucleotides were synthesized in the University of Florida ICBR DNA Synthesis Laboratory (University of Florida, Gainesville, Fla.) and end-labeled with digoxigenin in a reaction using terminal transferase. The digoxigenin labeled oligonucleotides were hybridized to the immobilized PCR products under conditions of high stringency (5X SSC and 68° C.). Hybridization was detected colorimetrically by enzyme-linked immunosorbent assay (ELISA) with an anti-digoxigenin alkaline phosphatase conjugate according to the manufacturer's protocol provided with the GENIUS III kit (Boehringer Mannheim GmBH).

Generation of Genus-specific and Group-specific Probes

Preliminary studies looking at the efficacy of various oligonucleotide pairs to amplify portions of the oxc gene present in various O. formigenes strains revealed that the PCR primer pair AP34 (5'-primer)/Ap21 (3'-primer) amplified a 500 bp DNA fragment in both group I and group II strains. To determine the degree of sequence homology within the 5'-end of the oxc gene between various strains of O. formigenes, genomic DNA was prepared from 5 group I and 7 group II strains isolated from human fecal samples for use as template in PCR with AP34 and AP21. Each PCR amplified an expected 500 bp product that was subsequently cloned into the pCR-2.1 vector system and sequenced. A comparison of the 5'-end sequences of the oxc gene from these 12 human isolates with the OxB gene is shown in part in FIGS. 9A–9B. The 5'-end of the oxc gene appears to be relatively conserved for a bacterial gene, with most bp changes occurring in the wobble base such that the codon translation is not altered. Nevertheless, there were enough sequence differences to demarcate group I strains from group II strains, thus permitting selection of regions that are conserved within strains of a specific group, but differ significantly from strains of the other group. Based on these conserved regions, genus-specific oligonucleotide probes (for example, probe AP286, homologous to the region between bp 13 and 43 of the open-reading frame), as well as group I-specific (for example, probe HS2, homologous to the region between bp 197 and 214 of the open-reading frame) and group II-specific (for example, probe AP307, homologous to the region between bp 133 and 150 of the open-reading frame) probes were prepared.

Specificity of the Genus-specific and Group-specific Oligonucleotide Probes

Figure 10A:
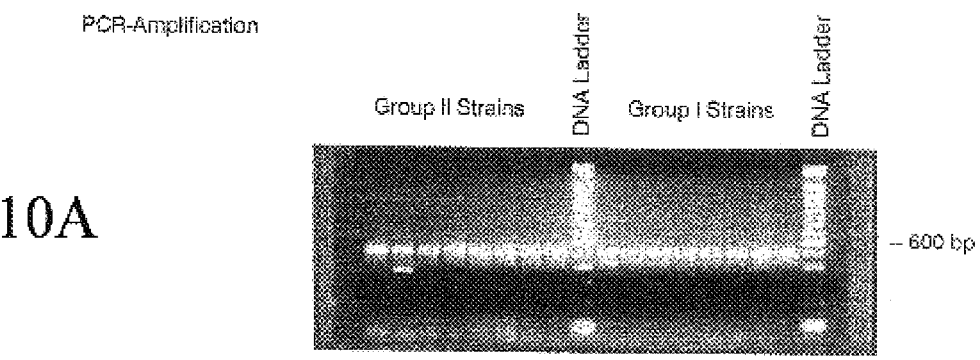
FIGS. 10A–10B show the detection of *Oxalobacter formigenes* using a genus-specific oligonucleotide probe that hybridizes to the PCR product of the oxc gene. Using the primer pair AP34/AP21, PCR amplification was performed using genomic template DNA isolated from 8 group I and 8 group II strains of *O. formigenes*. The PCR products were size fractionated by electrophoresis through 1.2% agarose gels and the expected 504–508 bp product visualized with EtBr under UV light (upper panel). The PCR products were transblotted to nylon membranes and Southern blotted using the genus-specific oligonucleotide probe, AP286 (lower panel).
Figure 10B:
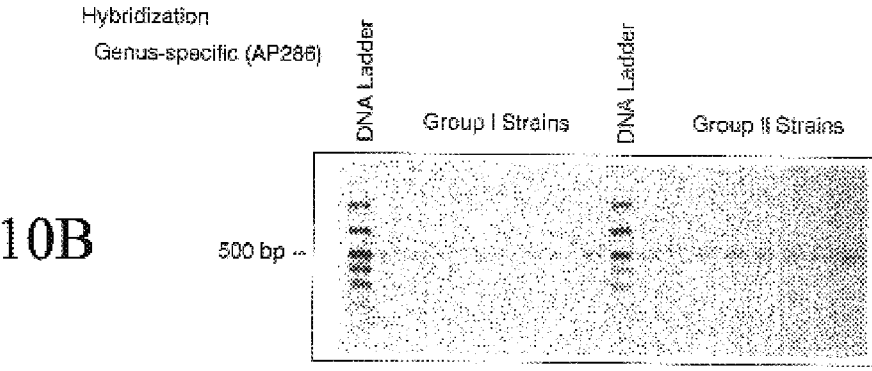

The specificity of probes AP286, AP307, and HS2 in detecting and classifying *O. formigenes* was examined using genomic DNA prepared from a number of known strains and isolates. PCR amplifications with the genus-specific primer pair AP34 and AP21 resulted in the 500 bp amplification product in all cultures tested (FIG. 10A, top panel). On Southern blotting, this 500 bp fragment hybridized with a genus-specific probe, AP286 (FIG. 10B, bottom panel).

Figure 11A:
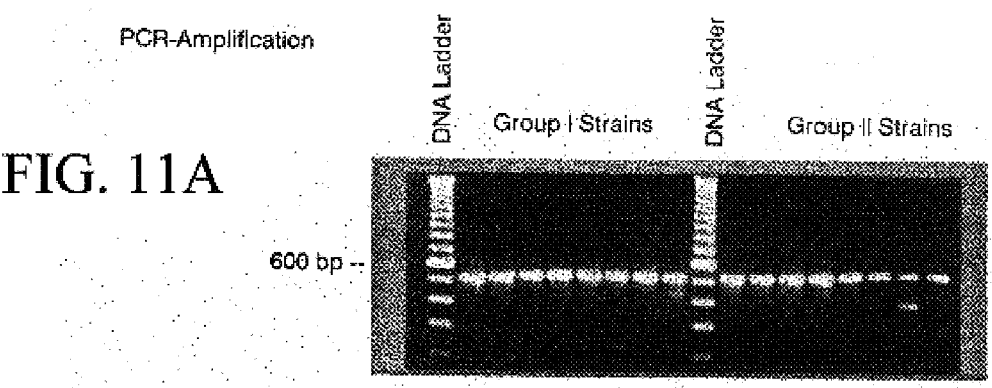
FIGS. 11A–11C show the classification of group I and group II strains of *Oxalobacter formigenes* using group-specific oligonucleotide probes that hybridize with PCR products of the oxc gene. Using the primer pair AP34/AP21, PCR amplification was performed using genomic template DNA isolated from 8 group I and 8 group II strains of *O. formigenes*. The PCR products were size fractionated by electrophoresis through 1.2% agarose gels and the expected 504–508 bp product visualized with EtBr under UV light (upper panel). The PCR products were transblotted to nylon membranes and Southern blotted using HS2, the group I-specific (center panel), or AP307, the group II-specific (lower panel), oligonucleotide probes.
Figure 11B:
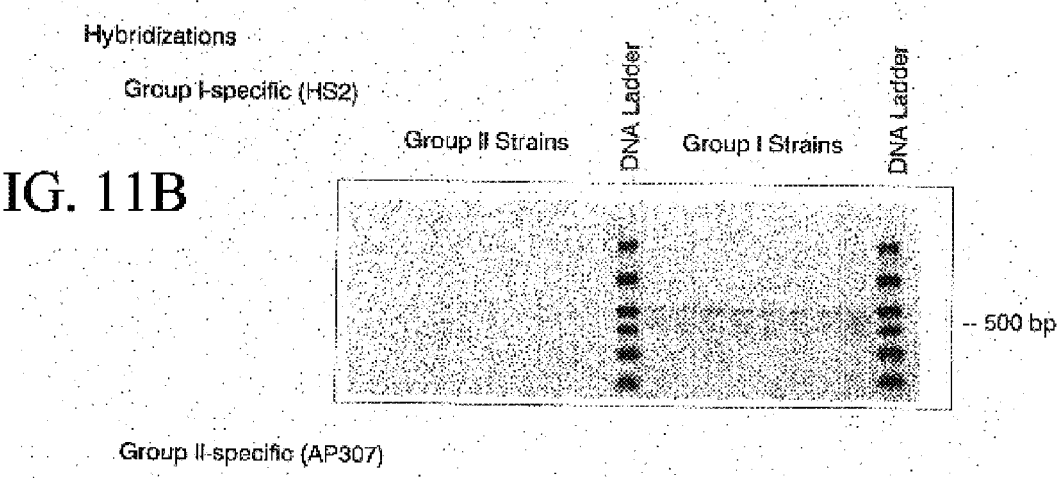
Figure 11C:
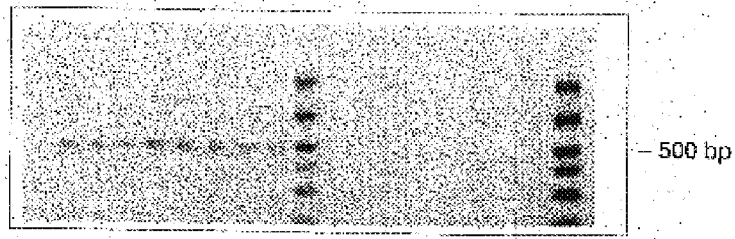

In a separate experiment, the amplified 500 bp PCR product was hybridized with either the group I-specific probe, HS2, (FIG. 11B, middle panel) or the group-specific probe, AP307, (FIG. 11C, bottom panel). Results clearly show a group specificity in the binding of these group-specific probes and their ability to identify subgroups of *O. formigenes*.

Application of a PCR-based Detection System for *O. formigenes* In a double-blinded study, 100 fecal samples were collected from children ranging in age from newborn to 12 years and tested for the presence of *O. formigenes* using both an oxalate degradation system and our PCR-based assay system. The aim of this study was to determine the age at which children become naturally colonized with this intestinal anaerobic bacterium. Of the 100 fecal samples examined, 72 samples tested positive for *O. formigenes* by PCR, 59 of which also exhibited oxalate degradation in an oxalate degradation assay. Interestingly, of the 72 positive samples, 68 were group II strains while only 4 were group I strains. All fecal cultures exhibiting degradation of oxalate tested positive for *O. formigenes* by PCR. Although there were 13 cultures that failed to degrade oxalate that proved positive for *O. formigenes* by PCR, the majority of the samples that failed to degrade oxalate also failed to exhibit amplification of a product in the PCR-reaction. These data show that the PCR-based assay is probably more sensitive than the biochemical (calcium chloride precipitation) test, yet highly specific.

When the data were unblinded, a clear pattern for the natural colonization of children became evident. *O. formigenes* could not be detected in infants less than 6–9 months of age. *O. formigenes* began appearing in the intestinal tracts of children around 1 year of age, and by 3–4 years of age, all children showed signs of being colonized. Although the sample size is small, the number of children colonized with *O. formigenes* declined between 8–12 years of age, reaching the colonization frequency of 70–80% estimated for adult populations (Doane et al., 1989, Kleinschmidt et al., 1993, Allison et al., 1986, and Goldkin et al., 1985).

EXAMPLE 4

Quantitative DNA-based detection and identification of *Oxalobacter formigenes*

Because the original PCR primer pair AP34/AP21 was based on the nucleotide sequence encoding oxalyl-CoA decarboxylase in strain OxB (isolated from sheep), a PCR primer pair based on conserved sequences found in human strains was used. This primer pair, OXF6 and OXF7, amplifies a 416 bp product. The nucleotide sequences of OXF6 and OXF7 are shown below:

```
OXF6   5'-AATGTAGAGTTGACTGA-3'    (SEQ ID NO. 12)

OXF7   5'-TTGATGCTGTTGATACG-3'    (SEQ ID NO. 13)
```

To develop a competitive DNA template for use as an internal control for QC-PCR, a 227 bp fragment of the oxalyl-CoA decarboxylase gene (oxc) flanked by sequences homologous for the OXF6/OXF7 primer pair and containing the genus-specific, group I-specific and group II-specific probe sites was generated. To accomplish this, a PCR reaction was performed using the OXF6 5'-primer plus a modified OXF7 3'-primer. The modified 3'-primer consisted of two portions: a 5'-end which contained the 3'-primer sequence within the oxc gene plus a 3'-end which annealed at a site located approximately 200 bp downstream of the 5'-primer site. The PCR using the primer pair OXF6/modified-OXF7 amplified the 210 bp segment and synthesized the 17 bp OXF7 primer site at the 3'-end. This PCR fragment was purified and ligated into pCR-2.1 (Invitrogen, Inc., San Diego, Calif.). A recombinant pCR-2.1 plasmid with the proper insert (confirmed by sequencing) was selected for use as the internal competitive template.

Figures 12A, 12B, 12C:
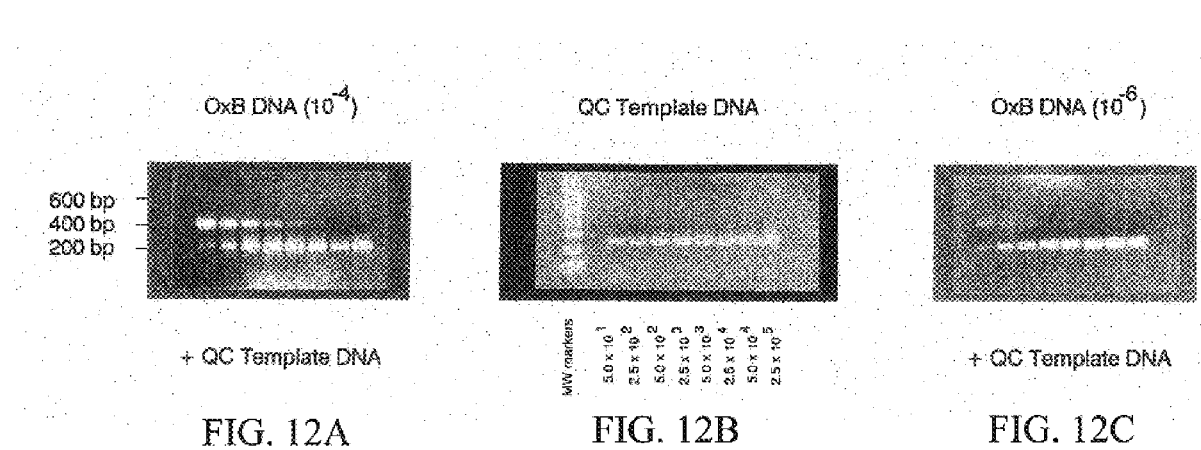
FIG. 12 shows agarose gels containing oxc amplification products from quantitative PCR visualized with UV light (FIGS. 12A–12C).
FIGS. 12D–12E show Log equivalence plots to determine the number of oxc molecules in the sample.

Quantitative PCR (QC-PCR) were performed as described below. Competitive template diluted from $1\times10^{10}$ to $1\times10^{2}$ copies/PCR were used to establish standard curves. Experimental PCRs were established containing both experimental *O. formigenes* DNA and dilutions of the synthetic template. The PCR products were size separated by electrophoresis through 1.5% agarose gels visualized with UV light and photographed (FIGS. 12A–12C). Photographs were scanned for relative band intensities, normalized for differences in molecular mass, and plotted against the log of the copy number of synthetic template added per reaction.

Figure 12D:
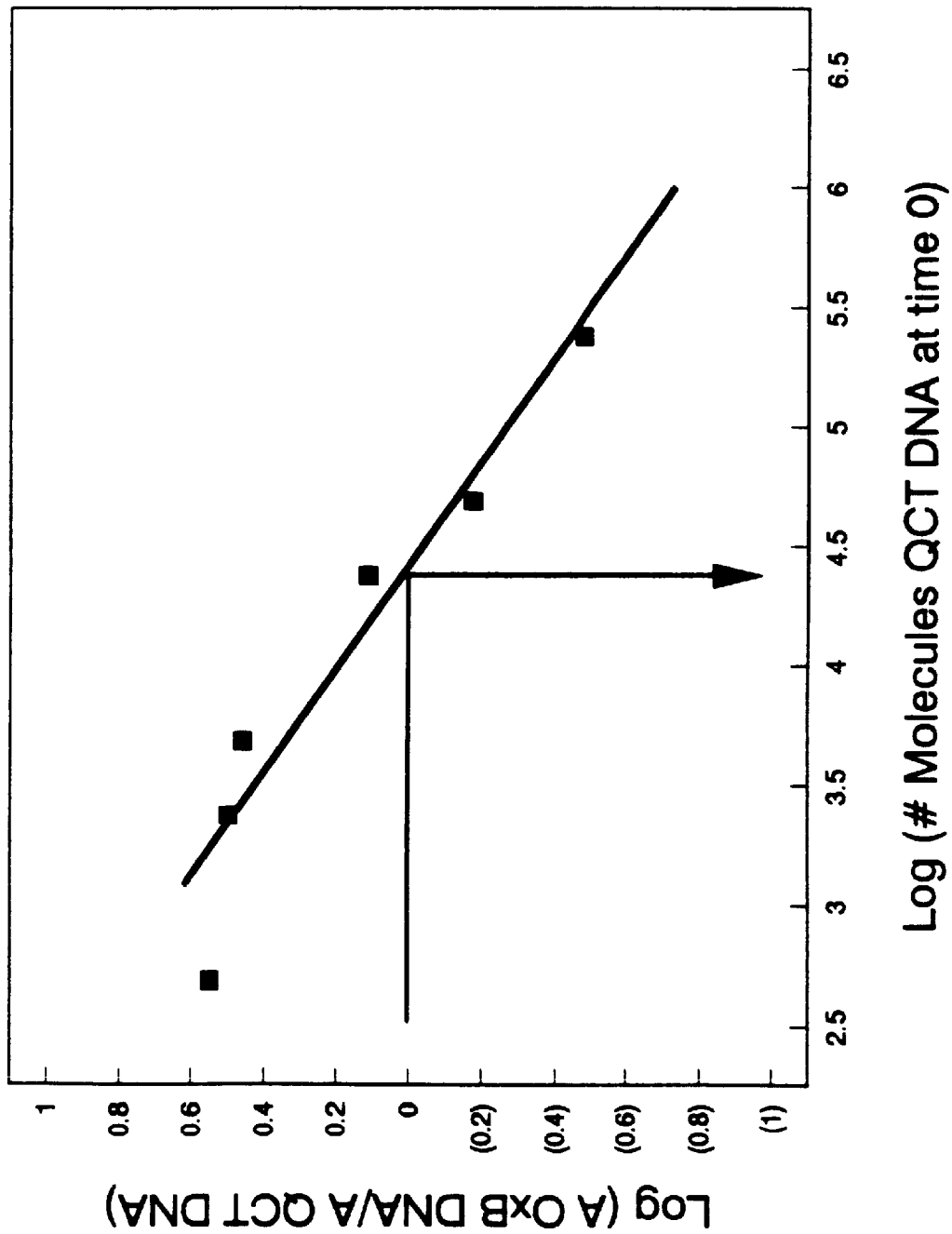
Figure 12E:
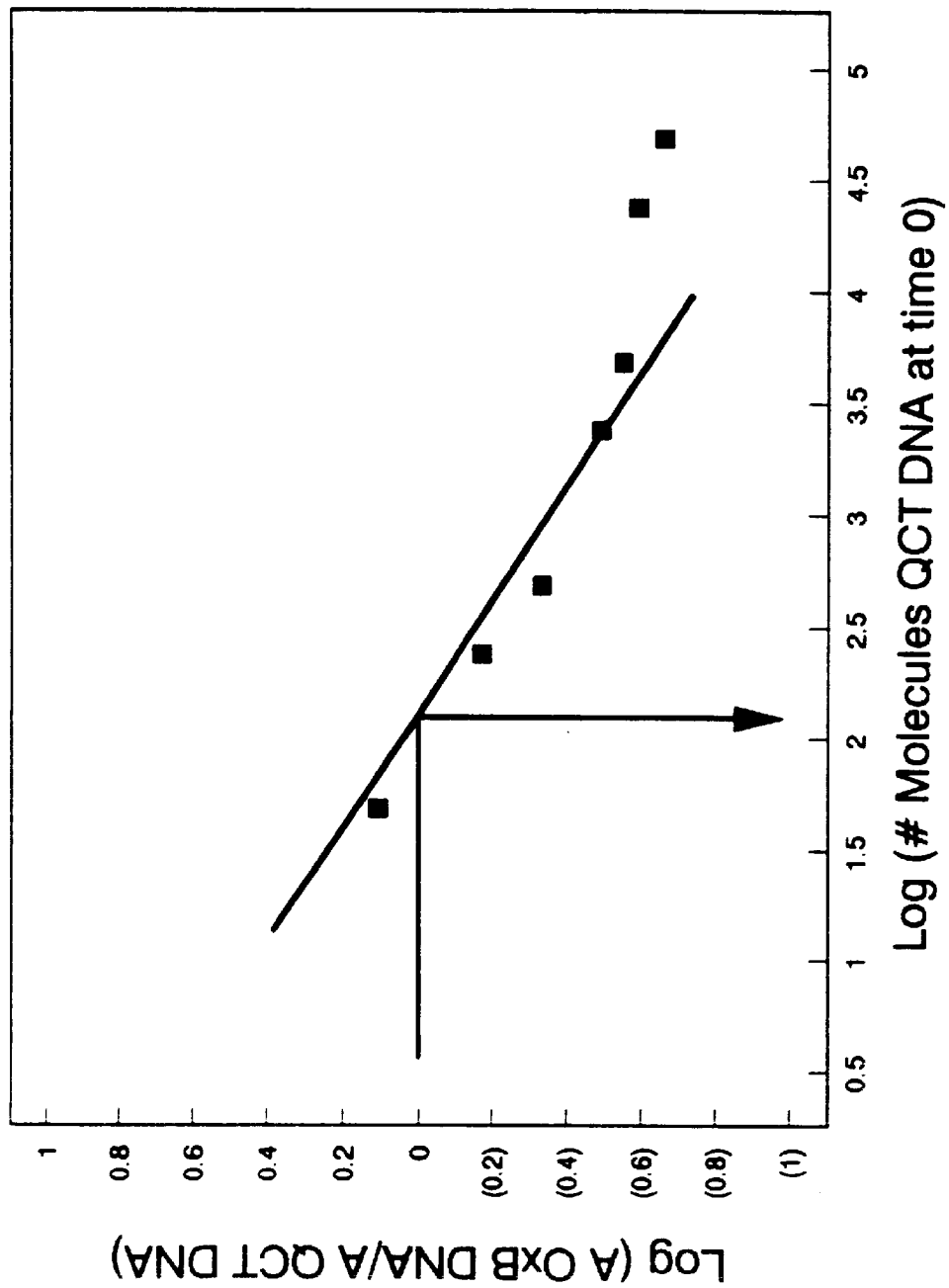

Quantitation of the number of oxc genes, thereby the number of bacteria in a sample, revealed the accuracy of this QC-PCR detection system. Assuming the genome of *O. formigenes* is similar in size to that of *E. coli* ($4.7\times10^{3}$ Kb), then 1 $\mu$g of genomic DNA would contain $1.8\times10^{8}$ molecules (or gene copies). Genomic DNA prepared from *O. formigenes* OxB had a concentration by spectrophotometric analysis of 1.126 $\mu$g DNA/$\mu$l or $2\times10^{8}$ molecules/$\mu$l. Two dilutions, $10^{-4}$ (20,000 molecules) and $10^{-6}$ (200 molecules) of this DNA were used as template in the QC-PCR with dilutions of competitive template ranging from 50 to 250,000 molecules. As shown in FIGS. 12D–12E, the Log equivalence revealed that the number of molecules of *O. formigenes* OxB in the reaction were estimated between 19,900–25,100 and 126–158.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Allison, M. J., H. M. Cook, D. B. Milne, S. Gallaher, R. V. Clayman (1986) "Oxalate degradation by gastrointestinal bacteria from humans," *J Nutr* 116:455–460.

Allison, M. J., K. A. Dawson, W. R. Mayberry, J. G. Foss (1985) "*Oxalobacter formigenes* gen. nov., sp. nov.: oxalate degrading bacteria that inhabit the gastrointestinal tract," *Arch Microbiol.* 141:1–7.

Anderson, J. T., J. G. Comellius, A. J. Jarpe, W. E. Winter, A. B. Peck (1993) "Insulin-dependent diabetes in the NOD mouse model. II. β cell destruction in autoimmune diabetes is a $T_{H1}$ mediated event," *Autoimmunity* 15:113–122.

Argenzio, R. A., J. A. Liacos, M. J. Allison (1988) "Intestinal oxalate degrading bacteria reduce oxalate absorption and toxicity in guinea pigs," *J Nutr* 118:787–791.

Baetz, A. L., M. J. Allison (1989) "Punfication and Characterization of Oxalyl-Coenzyme A Decarboxylase from *Oxalobacter formigenes*," *J. Bacteriol.* 171:2605–2608.

Baetz, A. L., M. J. Allison (1990) "Purification and Characterization of Formyl-Coenzyme A Transferase from *Oxalobacter formigenes*," *J. Bacteriol.* 172:3537–3540.

Costello, J., M. Hatch, E. Bourke (1976) "An enzymic method for the spectrophotometric determination of oxalic acid," *J. Lab. Clin. Med.* 87(5):903–908.

Curhan, et al. (1993) "A Prospective study of dietary calcium and other nutrients and the risk of symptomatic kidney stones," *N.E.J. Med.* 328:833–838.

Daniel, S. L., P. A. Hartman, M. J. Allison (1987) "Microbial degradation of oxalate in the gastrointestinal tracts of rats," *Appl Environ Microbiol* 53:957–964.

Dawson, K. A., M. J. Allison, P. A. Hartman (1980) "Characteristics of anaerobic oxalate-degrading bacteria from the rumen," *Applied Microbiol.* 22:522–529.

Dawson, K. A., M. J. Allison, P. A. Hartman (1980) "Isolation and some characteristics of anaerobic oxalate-degrading bacteria from ruman" *Appl. Environ. Microbiol.* 40:833–839.

Doane, L. A., M. Liebman, D. R. Caldwell (1989) "Microbial oxalata degradation: effects on oxalate and calcium balance in humans," *Nutrition Res* 9:957–964.

Goldkin, L., D. R. Cave, B. Jaffin, W. Robinson, C. M. Bliss (1985) "A new factor in enteric hyperoxaluria: *Oxalobacter formigenes*" *AMJ Gastro* 80:860.

Hatch, M., R. W. Freel (1996) "Oxalate transport across intestinal and renal epithelia" *Calcium Oxalate in Biological Systems*, pages 217–238, CRC Press, Boca Raton, Fla.

Hodgkinson, A. (1970) "Determination of Oxalic acid in Biological Material," *Clin. Chem.* 16(7):547–557.

Jensen, N. S., M. J. Allison (1994) "Studies on the diversity among anaerobic oxalate-degrading bacteria now in the species *Oxalobacter formigenes*" *Abst. Ann. Mtg. Amer. Soc. Microbial.*, pages 1–29.

Jordan, J. A., M. B. Durso (1996) "Rapid speciation of the five most medically relevant candida species using PCR amplification and a microtitre plate-based detection system," *Mol Diagnosis* 1:51–58.

Kleinschmidt K., A. Mahlmann, R. Hautmann (1993) "Anaerobic oxalate-degrading bacteria in the gut decrease faecal and urinary oxalate concentrations in stone formers," In R. Ryall, R. Bais, V. R. Marshall, A. M. Rofe, L. H. Smith, V. R. Walker *Urolithiasis* 2, Plenum Press, New York, pp. 439–441.

Lung, H., A. L. Baetz, A. B. Peck (1994) "Molecular Cloning, DNA Sequence and Gene Expression of the Oxalyl-CoA Decarboxylase Gene, oxc, from the Bacterium *Oxalobacter formigenes*," *J. Bacteriol.* 176(8):2468–2472.

Maniatis, T., E. F. Fritsch, J. Sambrook (1989) *Molecular Cloning: A Laboratory Manual*, 2d Edition, Cold Spring Harbor Laboratory, Cold Spring Harbor, N.Y.

Smith, R. L., F. E. Strohmaier, R. S. Oremland (1985) "Isolation of anaerobic oxalate-degrading bacteria from fresh water lake sediments," *Arch Microbiol* 141:8–13.

Stacy-Phips, S., J. J. Mecca, J. B. Weiss (1995) "Multiplex PCR assay and simple preparation method for stool specimens detect enterotoxigenic *E. coli* DNA during course of infection," *J. Clin. Microbiol.* 33:1054–1059.

Tarnuzzer, R. W., S. P. Macauley, W. Farmerie, S. Cabellaro, M. R. Ghassemifar, C. Robinson, M. B. Grant, M. G. Humphreys-Beher, L. Franzen, A. B. Peck, and G. S. Schultz (1996) "Competitive RNA templates for detection and quantitation of growth factors, cytokines, extracellular matrix components and matrix metalloproteinases by RT-PCR," *Biotechnology* 20:670–674.

Yriberri, J., L. S. Posten (1980) "A semi-automatic enzymic method for estimating urinary oxalate," *Clin. Chem.* 26(7):881–884

---

We claim:

1. A method for detecting *Oxalobacter formigenes* in a sample, comprising the steps of:
   (a) contacting said sample with a polynucleotide probe under conditions sufficient for selective hybridization of said polynucleotide probe with DNA of *Oxalobacter formigenes* that comprises a nucleotide sequence of an oxalyl-CoA decarboxylase gene, wherein said polynucleotide probe is substantially complementary with a nucleotide sequence of an oxalyl-CoA decarboxylase gene of *Oxalobacter formigenes*; and
   (b) detecting said probe hybridized to said DNA.

2. The method according to claim 1, wherein said polynucleotide probe or said DNA is immobilized on a solid phase matrix prior to performing step (a).

3. The method according to claim 1, wherein said solid phase matrix is selected from the group consisting of paper, nitrocellulose, nylon, PVDF, and plastic.

4. The method according to claim 1, wherein said polynucleotide probe is labeled with a detectable label.

5. The method according to claim 4, wherein said detectable label is selected from the group consisting of a radioisotope, fluorophore, chemiluminescent molecule, and an enzyme.

6. The method according to claim 4, wherein said polynucleotide probe is labeled with fluorescein, rhodamine, luciferin, or luminol.

7. The method according to claim 5, wherein said enzyme is selected from the group consisting of horseradish peroxidase and alkaline phosphatase.

8. The method according to claim 1, wherein said polynucleotide probe is conjugated with a ligand, hapten, or antigenic determinant.

9. The method according to claim 8, wherein prior to step (b), said polynucleotide probe is contacted with a molecule that binds to said ligand, hapten, or antigenic determinant, wherein said molecule is detectably labeled.

10. The method according to claim 9, wherein said detectable label is selected from the group consisting of radioisotope, fluorophore, chemiluminescent molecule, and an enzyme.

11. The method according to claim 1, wherein said polynucleotide probe comprises a nucleotide sequence selected from the group consisting of SEQ ID NO. 5, SEQ ID NO. 6, SEQ ID NO. 9, SEQ ID NO. 14, SEQ ID NO. 15, and SEQ ID NO. 16, or a fragment of said nucleotide sequence which can selectively hybridize with DNA of *Oxalobacter formigenes* in step (a).

12. The method according to claim 1, wherein said polynucleotide probe comprises the nucleotide sequence of SEQ ID NO. 14.

13. A method for detecting *Oxalobacter formigenes* in a sample, comprising the steps of:
   (a) amplifying DNA of *Oxalobacter formigenes* by polymerase chain reaction (PCR) using a polynucleotide PCR primer, wherein said primer is substantially complementary with a polynucleotide sequence comprising an oxalyl-CoA decarboxylase gene of *Oxalobacter formigenes*;
   (b) contacting said amplified DNA with a polynucleotide probe under conditions sufficient for selective hybridization of said polynucleotide probe with DNA of *Oxalobacter formigenes* that comprises a nucleotide sequence of an oxalyl-CoA decarboxylase gene, wherein said polynucleotide probe is substantially complementary with a nucleotide sequence of an oxalyl-CoA decarboxylase gene of *Oxalobacter formigenes*; and
   (c) detecting said probe hybridized to said DNA.

14. The method according to claim 13, wherein said amplified DNA is immobilized on a solid phase matrix prior to performing step (b).

15. The method according to claim 13, wherein said polynucleotide probe is immobilized as a solid phase matrix prior to performing step (b).

16. The method according to claim 13, wherein said primer comprises a nucleotide sequence selected from the group consisting of SEQ ID NO. 6, SEQ ID NO. 7, SEQ ID NO. 8, SEQ ID NO. 9, SEQ ID NO. 11, SEQ ID NO. 12, SEQ ID NO. 13, and SEQ ID NO. 17, or a fragment of said nucleotide sequence which can prime said PCR amplification in step (a).

17. The method according to claim 13, wherein said primer comprises a nucleotide sequence selected from the group consisting of SEQ ID NO. 12 and SEQ ID NO. 13.

18. The method according to claim 14, wherein said solid phase matrix is selected from the group consisting of paper, nitrocellulose, nylon, PVDF, and plastic.

19. The method according to claim 15, wherein said solid phase matrix is selected from the group consisting of paper, nitrocellulose, nylon, PVDF, and plastic.

20. The method according to claim 13, wherein said polynucleotide probe is labeled with a detectable label.

21. The method according to claim 20, wherein said detectable label is selected from the group consisting of a radioisotope, fluorophore, chemiluminescent molecule, and an enzyme.

22. The method according to claim 21, wherein said enzyme is selected from the group consisting of horseradish peroxidase and alkaline phosphatase.

23. The method according to claim 13, wherein said polynucleotide probe is conjugated with a ligand, hapten, or antigenic determinant.

24. The method according to claim 23, wherein prior to step (b), said polynucleotide probe is contacted with a molecule that binds to said ligand, hapten, or antigenic determinant, wherein said molecule is detectably labeled.

25. The method according to claim 24, wherein said detectable label is selected from the group consisting of radioisotope, fluorophore, chemiluminescent molecule, and an enzyme.

26. The method according to claim 13, wherein said PCR primer is labeled with a detectable label.

27. The method according to claim 26, wherein said detectable label is selected from the group consisting of a radioisotope, fluorophore, chemiluminescent molecule, and an enzyme.

28. The method according to claim 13, wherein said PCR primer is conjugated with a ligand, hapten, or antigenic determinant.

29. The method according to claim 28, wherein prior to step (c), said PCR primer is contacted with a molecule that binds to said ligand, hapten, or antigenic determinant, wherein said molecule is detectably labeled.

30. The method according to claim 29, wherein said detectable label is selected from the group consisting of radioisotope, fluorophore, chemiluminescent molecule, and an enzyme.

31. The method according to claim 13, wherein said polynucleotide probe comprises a nucleotide sequence selected from the group consisting of SEQ ID NO. 5, SEQ ID NO. 6, SEQ ID NO. 9, SEQ ID NO. 14, SEQ ID NO. 15, and SEQ ID NO. 16, or a fragment of said nucleotide sequence which can selectively hybridize with DNA of *Oxalobacter formigenes* in step (b).

32. The method according to claim 13, wherein said polynucleotide probe comprises the nucleotide sequence of SEQ ID NO. 14.

33. A polynucleotide probe that selectively hybridizes with DNA of *Oxalobacter formigenes*, comprising a nucleotide sequence that is substantially complementary with a polynucleotide sequence present in an *Oxalobacter formigenes* genome, wherein the polynucleotide sequence present in the *Oxalobacter formigenes* genome comprises a gene selected from the group consisting of the formyl-CoA transferase gene and the oxalyl-CoA decarboxylase gene.

34. The polynucleotide probe, according to clam 33, wherein said polynucleotide probe hybridizes under high-stringency conditions with a nucleotide sequence of said formyl-CoA transferase gene or said oxalyl-CoA decarboxylase gene.

35. An oligonucleotide comprising a nucleotide sequence that is substantially complementary with a polynucleotide sequence present in an *Oxalobacter formigenes* genome, wherein said polynucleotide sequence present in said *Oxalobacter formigenes* genome comprises a gene selected from the group consisting of the formyl-CoA transferase gene and the oxalyl-CoA decarboxylase gene, and wherein said oligonucleotide is capable of priming polymerase chain reaction amplification of said polynucleotide sequence present in said *Oxalobacter formigenes* genome.

36. A kit for detecting the presence of *Oxalobacter formigenes* in a sample, comprising in one or more separate containers:

(a) the polynucleotide probe according to claim 33.

37. The kit, according to claim 36, further comprising:

(b) an oligonucleotide comprising a nucleotide sequence that is substantially complementary with a polynucleotide sequence present in an *Oxalobacter formigenes* genome, wherein said polynucleotide sequence present in said *Oxalobacter formigenes* genome comprises a gene selected from the group consisting of the formyl-CoA transferase gene and the oxalyl-CoA decarboxylase gene, and wherein said oligonucleotide is capable of priming polymerase chain reaction amplification of said polynucleotide sequence present in said *Oxalobacter formigenes* genome.

38. The method according to claim 1, further comprising after step (a), a washing step to remove non-hybridized material.

39. The method according to claim 1, wherein said sample is treated to fragment DNA in said sample prior to contact with said polynucleotide probe.

40. The method according to claim 39, wherein DNA in said sample is fragmented by contacting said sample with a restriction endonuclease.

41. The method according to claim 1, wherein said sample is a biological sample.

42. The method according to claim 41, wherein said biological sample is selected from the group consisting of biopsy, fecal matter, and tissue scrapings.

43. The method according to claim 1, wherein said sample is treated to isolate DNA from organisms present in said sample.

44. The method according to claim 13, further comprising after step (b), a washing step to remove non-hybridized material.

45. The method according to claim 13, wherein said sample is treated to fragment DNA in said sample prior to contact with said polynucleotide probe or amplification with said polynucleotide PCR primer.

46. The method according to claim 45, wherein DNA in said sample is fragmented by contacting said sample with a restriction endonuclease.

47. The method according to claim 13, wherein said sample is a biological sample.

48. The method according to claim 47, wherein said biological sample is selected from the group consisting of biopsy, fecal matter, and tissue scrapings.

49. The method according to claim 13, wherein said sample is treated to isolate DNA from organisms present in said sample.

* * * * *

UNITED STATES PATENT AND TRADEMARK OFFICE
CERTIFICATE OF CORRECTION

PATENT NO. : 6,709,820 B2
DATED : March 23, 2004
INVENTOR(S) : Ammon B. Peck and Harmeet Sidhu It is certified that error appears in the above-identified patent and that said Letters Patent is hereby corrected as shown below:

Column 3,
Line 36, "calorimetrically" should read -- colorimetrically --.

Column 11,
Line 47, "or $^{32}$p" should read -- or $^{32}$P --.

Column 13,
Line 58, "A340" should read -- $A_{340}$ --.

Column 15,
Line 11, "calorimetrically" should read -- colorimetrically --.

Column 19,
Line 13, "group-specific" should read -- group II-specific --.

Column 20,
Line 57, "Comellius" should read -- Cornellius --.

Column 22,
Line 26, "Tarnuzzer" should read -- Tarmuzzer --.

Signed and Sealed this

Twenty-ninth Day of June, 2004

JON W. DUDAS
*Acting Director of the United States Patent and Trademark Office*

SEQUENCE LISTING

<160> NUMBER OF SEQ ID NOS: 19

<210> SEQ ID NO 1
<211> LENGTH: 1577
<212> TYPE: DNA
<213> ORGANISM: Oxalobacter formigenes

<400> SEQUENCE: 1

```
aagcttgctt cattttgaga tgttatgcga agtgttagca acccaagtta gtacccttca      60
gccctttggg cgaagttttt ctttcttggc agttcctttc ggggaaacag cacagagaat     120
aaaaaccaaa agttgtacca acgacaagga aatgagaaat tatgactaaa ccattagatg     180
gaattaatgt gcttgacttt acccacgtcc aggcaggtcc tgcctgtaca cagatgatgg     240
gtttcttggg cgcaaacgtc atcaagattg aaagacgtgg ttccggagat atgactcgtg     300
gatggctgca ggacaaacca aatgttgatt ccctgtattt cacgatgttc aactgtaaca     360
aacgttcgat tgaactggac atgaaaaccc cggaaggcaa agagcttctg gaacagatga     420
tcaagaaagc cgacgtcatg gtcgaaaact tcggaccagg cgcactggac cgtatgggct     480
ttacttggga atacattcag gaactgaatc cacgcgtcat tctggcttcc gttaaaggct     540
atgcagaagg ccacgccaac gaacacctga agtttatga aaacgttgca cagtgttccg     600
gcggtgctgc agctaccacc ggtttctggg atggtcctcc aaccgtttcc ggcgctgctc     660
```

-continued

```
tgggtgactc caactccggt atgcacctga tgatcggtat tctggccgct ctggaaatgc    720
gtcacaaaac cggccgtggt cagaaagttg ccgtcgctat gcaggacgct gttctgaatc    780
tggttcgtat caaactgcgt gaccagcaac gtctggaaag aaccggcatt ctggctgaat    840
acccacaggc tcagcctaac tttgccttcg acagagacgg taacccactg tccttcgaca    900
acatcacttc cgttccacgt ggtggtaacg caggtggcgg cggccagcca ggctggatgc    960
tgaaatgtaa aggttgggaa accgatgcgg actcctacgt ttacttcacc atcgctgcaa   1020
acatgtggcc acagatctgc gacatgatcg acaagccaga atggaaagac gacccagcct   1080
acaacacatt cgaaggtcgt gttgacaagc tgatggacat cttctccttc atcgaaacca   1140
agttcgctga caaggacaaa ttcgaagtta ccgaatgggc tgcccagtac ggcattcctt   1200
gcggtccggt catgtccatg aaagaactgg ctcacgatcc ttccctgcag aaagttggta   1260
ccgtcgttga agttgtcgac gaaattcgtg taaccacct gaccgttggc gcaccgttca   1320
aattctccgg attccagccg gaaattaccc gtgctccgct gttgggcgaa cataccgacg   1380
aagttctgaa agaactgggt cttgacgatg ccaagatcaa ggaactgcat gcaaaacagg   1440
tagtttgatc cgtcagactt tctgggcaaa cggcactct ccggagtgcc gttttttgtc   1500
acacgaaacc taatcaaaca agcacgtgca atgattccac atcattgcgg ccacattcat   1560
ccttcgggtc attactg                                                  1577
```

<210> SEQ ID NO 2
<211> LENGTH: 428
<212> TYPE: PRT
<213> ORGANISM: Oxalobacter formigenes

<400> SEQUENCE: 2

```
Met Thr Lys Pro Leu Asp Gly Ile Asn Val Leu Asp Phe Thr His Val
1               5                  10                  15

Gln Ala Gly Pro Ala Cys Thr Gln Met Met Gly Phe Leu Gly Ala Asn
            20                  25                  30

Val Ile Lys Ile Glu Arg Arg Gly Ser Gly Asn Met Thr Arg Gly Trp
        35                  40                  45

Leu Gln Asp Lys Pro Asn Val Asp Ser Leu Tyr Phe Thr Met Phe Asn
    50                  55                  60

Cys Asn Lys Arg Ser Ile Glu Leu Asp Met Lys Thr Pro Glu Gly Lys
65                  70                  75                  80

Glu Leu Leu Glu Gln Met Ile Lys Lys Ala Asp Val Met Val Glu Asn
                85                  90                  95

Phe Gly Pro Gly Ala Leu Asp Arg Met Gly Phe Thr Trp Glu Tyr Ile
            100                 105                 110

Gln Glu Leu Asn Pro Arg Val Ile Leu Ala Ser Val Lys Gly Tyr Ala
        115                 120                 125

Glu Gly His Ala Asn Glu His Leu Lys Val Tyr Glu Asn Val Ala Gln
    130                 135                 140

Cys Ser Gly Gly Ala Ala Ala Thr Thr Gly Phe Trp Asp Gly Pro Pro
145                 150                 155                 160

Thr Val Ser Gly Ala Ala Leu Gly Asp Ser Asn Ser Gly Met His Leu
                165                 170                 175

Met Ile Gly Ile Leu Ala Ala Leu Glu Met Arg His Lys Thr Gly Arg
            180                 185                 190

Gly Gln Lys Val Ala Val Ala Met Gln Asp Ala Val Leu Asn Leu Val
        195                 200                 205
```

```
Arg Ile Lys Leu Arg Asp Gln Arg Leu Glu Arg Thr Gly Ile Leu
    210                 215                 220

Ala Glu Tyr Pro Gln Ala Gln Pro Asn Phe Ala Phe Asp Arg Asp Gly
225                 230                 235                 240

Asn Pro Leu Ser Phe Asn Asn Ile Thr Ser Val Pro Arg Gly Gly Asn
                245                 250                 255

Ala Gly Gly Gly Gly Glu Pro Gly Trp Met Leu Lys Cys Lys Gly Trp
            260                 265                 270

Glu Thr Asp Ala Asp Ser Tyr Val Tyr Phe Thr Ile Ala Ala Asn Met
        275                 280                 285

Trp Pro Gln Ile Cys Asn Met Ile Asp Lys Pro Glu Trp Lys Asp Asp
    290                 295                 300

Pro Ala Tyr Asn Thr Phe Glu Gly Arg Val Asp Lys Leu Met Asp Ile
305                 310                 315                 320

Phe Ser Phe Ile Glu Thr Lys Phe Ala Asp Lys Asp Lys Phe Glu Val
                325                 330                 335

Thr Glu Trp Ala Ala Gln Tyr Gly Ile Pro Cys Gly Pro Val Met Ser
            340                 345                 350

Met Lys Glu Leu Ala His Asp Pro Ser Leu Gln Lys Val Gly Thr Val
        355                 360                 365

Val Glu Val Val Asp Glu Ile Arg Gly Asn His Leu Thr Val Gly Ala
    370                 375                 380

Pro Phe Lys Phe Ser Gly Phe Gln Pro Glu Ile Thr Arg Ala Pro Leu
385                 390                 395                 400

Leu Gly Glu His Thr Asp Glu Val Leu Lys Glu Leu Gly Leu Asp Asp
                405                 410                 415

Ala Lys Ile Lys Glu Leu His Ala Lys Gln Val Val
                420                 425

<210> SEQ ID NO 3
<211> LENGTH: 2088
<212> TYPE: DNA
<213> ORGANISM: Oxalobacter formigenes

<400> SEQUENCE: 3
atttgtttaa attgacctga atcaatattg ccggattgat ctaggtcaat gaatgcaaat      60
tgacttatgt caatggtgcc aaattgacct aggtcaacgg gattttttaaa gggtatgcgg    120 catactcgga attgacgtta aacaacgttt atcaaaacca accaaagaaa ggtattactc     180
atgagtaacg acgacaatgt agagttgact gatggctttc atgttttgat cgatgccctg    240
aaaatgaatg acatcgatac catgtatggt gttgtcggca ttcctatcac gaacctggct    300
cgtatgtggc aagatgacgg tcagcgtttt tacagcttcc gtcacgaaca cacgcaggt    360 tatgcagctt ctatcgccgg ttacatcgaa ggaaaacctg cgtttgctt gaccgttcc     420 gcccctggct tcctgaacgg cgtgacttcc ctggctcatg caaccaccaa ctgcttccca    480
atgatcctgt tgagcggttc cagtgaacgt gaaatcgtcg atttccaaga cggcgattac    540
gaagaaatgg atcagatgaa tgttgcacgt ccacactgca aagcttcttt ccgtatcaac    600
agcatcaaag acattccaat cggtatcgct cgtgcagttc gcaccgctgt atccggacgt    660
ccaggtggtg tttacgttga cttcccagca aaactgttcg gtcagaccat ttctgtagaa    720
gaagctaaca actgctcttt caaaccaatc gatccagctc cggcacagat tcttgctgaa    780
gacgctatcg ctcgcgctgc tgacctgatc aagaacgcca acgtccagt tatcatgctg    840 ggtaaaggcg ctgcatacgc acaatgcgac gacgaaatcc gcgcactggt tgaagaaacc    900
```

```
ggcatcccat tcctgccaat gggtatggct aaaggcctgc tgcctgacaa ccatccacaa      960
tccgctgctg caacccgtgc tttcgcactg gcacagtgtg acgtttgcgt actgatcggc     1020
gctcgtctga actggctgat gcagcacggt aaaggcaaaa cctggggcga cgaactgaag     1080
aaatacgttc agatcgacat ccaggctaac gaaatggaca gcaaccagcc tatcgctgca     1140
ccagttgttg gtgacatcaa gtccgccgtt tccctgctcc gcaaagcact gaaaggcgct     1200
ccaaaagctg acgctgaatg gaccggcgct ctgaaagcca agttgacgg caacaaagcc     1260 aaactggctg gcaagatgac tgccgaaacc ccatccggaa tgatgaacta ctccaattcc     1320
ctgggcgttg ttcgtgactt catgctggca atccggata tttccctggt aacgaaggc     1380 gctaatgcac tcgacaacac tcgtatgatt gttgacatgc tgaaaccacg caaacgtctt     1440
gactccggta cctggggtgt tatgggtatt ggtatgggct actgcgttgc tgcagctgct     1500
gttaccggca aaccggttat cgctgttgaa ggcgatagcg cattcggttt ctccggtatg     1560
gaactggaaa ccatctgccg ttacaacctg ccagttaccg ttatcatcat gaacaatggt     1620
ggtatctata aagtaacga agcagatcca caaccaggcg ttatctcctg tacccgtctg     1680
acccgtggtc gttacgacat gatgatggaa gcatttggcg gtaaaggtta tgttgccaat     1740
actccagcag aactgaaagc tgctctggaa gaagctgttg cttccggcaa accatgcctg     1800
atcaacgcga tgatcgatcc agacgctggt gtcgaatctg ccgtatcaa gagcctgaac     1860 gttgtaagta aagttggcaa gaaataatta gcccaacttt gatgaccggt tacgaccggt     1920
cacataaagt gttcgaatgc ccttcaagtt tacttgaagg gcattttttt accttgcagt     1980
ttataaacag gaaaaattgt attcagagcg gaaaagcaga tttaagccac gagaaacatt     2040
cttttttatt gaaaattgcc ataaacacat ttttaaagct ggctttt                   2088
```

<210> SEQ ID NO 4
<211> LENGTH: 568
<212> TYPE: PRT
<213> ORGANISM: Oxalobacter formigenes

<400> SEQUENCE: 4

```
Met Ser Asn Asp Asp Asn Val Glu Leu Thr Asp Gly Phe His Val Leu
1               5                   10                  15

Ile Asp Ala Leu Lys Met Asn Asp Ile Asp Thr Met Tyr Gly Val Val
                20                  25                  30

Gly Ile Pro Ile Thr Asn Leu Ala Arg Met Trp Gln Asp Asp Gly Gln
            35                  40                  45

Arg Phe Tyr Ser Phe Arg His Glu Gln His Ala Gly Tyr Ala Ala Ser
        50                  55                  60

Ile Ala Gly Tyr Ile Glu Gly Lys Pro Gly Val Cys Leu Thr Val Ser
65                  70                  75                  80

Ala Pro Gly Phe Leu Asn Gly Val Thr Ser Leu Ala His Ala Thr Thr
                85                  90                  95

Asn Cys Phe Pro Met Ile Leu Leu Ser Gly Ser Ser Glu Arg Glu Ile
                100                 105                 110

Val Asp Leu Gln Gln Gly Asp Tyr Glu Glu Met Asp Gln Met Asn Val
            115                 120                 125

Ala Arg Pro His Cys Lys Ala Ser Phe Arg Ile Asn Ser Ile Lys Asp
        130                 135                 140

Ile Pro Ile Gly Ile Ala Arg Ala Val Arg Thr Ala Val Ser Gly Arg
145                 150                 155                 160
```

-continued

```
Pro Gly Gly Val Tyr Val Asp Leu Pro Ala Lys Leu Phe Gly Gln Thr
            165                 170                 175
Ile Ser Val Glu Glu Ala Asn Lys Leu Leu Phe Lys Pro Ile Asp Pro
        180                 185                 190
Ala Pro Ala Gln Ile Pro Ala Glu Asp Ala Ile Ala Arg Ala Ala Asp
    195                 200                 205
Leu Ile Lys Asn Ala Lys Arg Pro Val Ile Met Leu Gly Lys Gly Ala
    210                 215                 220
Ala Tyr Ala Gln Cys Asp Asp Glu Ile Arg Ala Leu Val Glu Glu Thr
225                 230                 235                 240
Gly Ile Pro Phe Leu Pro Met Gly Met Ala Lys Gly Leu Leu Pro Asp
                245                 250                 255
Asn His Pro Gln Ser Ala Ala Thr Arg Ala Phe Ala Leu Ala Gln
                260                 265                 270
Cys Asp Val Cys Val Leu Ile Gly Ala Arg Leu Asn Trp Leu Met Gln
            275                 280                 285
His Gly Lys Gly Lys Thr Trp Gly Asp Glu Leu Lys Lys Tyr Val Gln
    290                 295                 300
Ile Asp Ile Gln Ala Asn Glu Met Asp Ser Asn Gln Pro Ile Ala Ala
305                 310                 315                 320
Pro Val Val Gly Asp Ile Lys Ser Ala Val Ser Leu Leu Arg Lys Ala
                325                 330                 335
Leu Lys Gly Ala Pro Lys Ala Asp Ala Glu Trp Thr Gly Ala Leu Lys
                340                 345                 350
Ala Lys Val Asp Gly Asn Lys Ala Lys Leu Ala Gly Lys Met Thr Ala
            355                 360                 365
Glu Thr Pro Ser Gly Met Met Asn Tyr Ser Asn Ser Leu Gly Val Val
    370                 375                 380
Arg Asp Phe Met Leu Ala Asn Pro Asp Ile Ser Leu Val Asn Glu Gly
385                 390                 395                 400
Ala Asn Ala Leu Asp Asn Thr Arg Met Ile Val Asp Met Leu Lys Pro
                405                 410                 415
Arg Lys Arg Leu Asp Ser Gly Thr Trp Gly Val Met Gly Ile Gly Met
                420                 425                 430
Gly Tyr Cys Val Ala Ala Ala Val Thr Gly Lys Pro Val Ile Ala
            435                 440                 445
Val Glu Gly Asp Ser Ala Phe Gly Phe Ser Gly Met Glu Leu Glu Thr
    450                 455                 460
Ile Cys Arg Tyr Asn Leu Pro Val Thr Val Ile Ile Met Asn Asn Gly
465                 470                 475                 480
Gly Ile Tyr Lys Gly Asn Glu Ala Asp Pro Gln Pro Gly Val Ile Ser
                485                 490                 495
Cys Thr Arg Leu Thr Arg Gly Arg Tyr Asp Met Met Met Glu Ala Phe
                500                 505                 510
Gly Gly Lys Gly Tyr Val Ala Asn Thr Pro Ala Glu Leu Lys Ala Ala
            515                 520                 525
Leu Glu Glu Ala Val Ala Ser Gly Lys Pro Cys Leu Ile Asn Ala Met
    530                 535                 540
Ile Asp Pro Asp Ala Gly Val Ser Gly Arg Ile Lys Ser Leu Asn
545                 550                 555                 560
Val Val Ser Lys Val Gly Lys Lys
                565
```

```
<210> SEQ ID NO 5
<211> LENGTH: 17
<212> TYPE: DNA
<213> ORGANISM: Oxalobacter formigenes

<400> SEQUENCE: 5
gagcgatacc gattgga                                                    17

<210> SEQ ID NO 6
<211> LENGTH: 17
<212> TYPE: DNA
<213> ORGANISM: Oxalobacter formigenes

<400> SEQUENCE: 6
gcacaatgcg acgacga                                                    17

<210> SEQ ID NO 7
<211> LENGTH: 17
<212> TYPE: DNA
<213> ORGANISM: Oxalobacter formigenes

<400> SEQUENCE: 7
caggttatgc agcttct                                                    17

<210> SEQ ID NO 8
<211> LENGTH: 17
<212> TYPE: DNA
<213> ORGANISM: Oxalobacter formigenes

<400> SEQUENCE: 8
ggatggttgt caggcag                                                    17

<210> SEQ ID NO 9
<211> LENGTH: 17
<212> TYPE: DNA
<213> ORGANISM: Oxalobacter formigenes

<400> SEQUENCE: 9
atactcggaa ttgacgt                                                    17

<210> SEQ ID NO 10
<211> LENGTH: 23
<212> TYPE: DNA
<213> ORGANISM: Oxalobacter formigenes

<400> SEQUENCE: 10
ttcatgtcca gttcaatcga acg                                             23

<210> SEQ ID NO 11
<211> LENGTH: 17
<212> TYPE: DNA
<213> ORGANISM: Oxalobacter formigenes

<400> SEQUENCE: 11
gtagttcatc attccgg                                                    17

<210> SEQ ID NO 12
<211> LENGTH: 17
<212> TYPE: DNA
<213> ORGANISM: Oxalobacter formigenes

<400> SEQUENCE: 12
aatgtagagt tgactga                                                    17
```

```
<210> SEQ ID NO 13
<211> LENGTH: 17
<212> TYPE: DNA
<213> ORGANISM: Oxalobacter formigenes

<400> SEQUENCE: 13
ttgatgctgt tgatacg                                                  17

<210> SEQ ID NO 14
<211> LENGTH: 31
<212> TYPE: DNA
<213> ORGANISM: Oxalobacter formigenes

<400> SEQUENCE: 14
gacaatgtag agttgactga tggctttcat g                                  31

<210> SEQ ID NO 15
<211> LENGTH: 18
<212> TYPE: DNA
<213> ORGANISM: Oxalobacter formigenes

<400> SEQUENCE: 15
caggatggtc agaagttc                                                 18

<210> SEQ ID NO 16
<211> LENGTH: 17
<212> TYPE: DNA
<213> ORGANISM: Oxalobacter formigenes

<400> SEQUENCE: 16
ccggttacat cgaagga                                                  17

<210> SEQ ID NO 17
<211> LENGTH: 17
<212> TYPE: DNA
<213> ORGANISM: Oxalobacter formigenes

<400> SEQUENCE: 17
tccaatcggt atcgctc                                                  17

<210> SEQ ID NO 18
<211> LENGTH: 21
<212> TYPE: DNA
<213> ORGANISM: Oxalobacter formigenes

<400> SEQUENCE: 18
tttacccacg tccaggcagg t                                             21

<210> SEQ ID NO 19
<211> LENGTH: 23
<212> TYPE: DNA
<213> ORGANISM: Oxalobacter formigenes

<400> SEQUENCE: 19
gcaagctaac ttgacctgta ctt                                           23
```